(12) United States Patent
Schiller et al.

(10) Patent No.: US 12,378,242 B2
(45) Date of Patent: *Aug. 5, 2025

(54) INHIBITING CREB BINDING PROTEIN (CBP)

(71) Applicant: FORMA Therapeutics, Inc., Watertown, MA (US)

(72) Inventors: Shawn E. R. Schiller, Haverhill, MA (US); Torsten Herbertz, Stow, MA (US); Hongbin Li, Madison, CT (US); Bradford Graves, Nutley, NJ (US); Steven Mischke, Waltham, MA (US); Angela West, Franklin, MA (US); Jennifer R. Downing, Clinton, MA (US); Anna Ericsson, Shrewsbury, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,112

(22) Filed: Feb. 10, 2022

(65) Prior Publication Data

US 2022/0162207 A1  May 26, 2022

Related U.S. Application Data

(63) Continuation of application No. 16/946,159, filed on Jun. 8, 2020, now Pat. No. 11,254,674, which is a continuation of application No. 16/457,596, filed on Jun. 28, 2019, now Pat. No. 10,870,648.

(60) Provisional application No. 62/819,490, filed on Mar. 15, 2019, provisional application No. 62/692,593, filed on Jun. 29, 2018.

(51) Int. Cl.
 *C07D 471/04* (2006.01)
(52) U.S. Cl.
 CPC ................. *C07D 471/04* (2013.01)
(58) Field of Classification Search
 CPC .................................................. C07D 471/04
 See application file for complete search history.

(56) References Cited

U.S. PATENT DOCUMENTS

| | | | |
|---|---|---|---|
| 5,138,089 A * | 8/1992 | Sabatelli | A61Q 17/04 560/14 |
| 6,011,029 A | 1/2000 | Ding et al. | |
| 7,101,869 B2 | 9/2006 | Blumenkopf et al. | |
| 7,709,489 B2 | 5/2010 | Aranyi et al. | |
| 9,211,333 B2 | 12/2015 | Zhang et al. | |
| 9,388,161 B2 * | 7/2016 | Bair | A61P 1/04 |
| 9,975,896 B2 | 5/2018 | Marineau et al. | |
| 10,870,648 B2 * | 12/2020 | Schiller | C07D 471/04 |
| 11,254,674 B2 * | 2/2022 | Schiller | A61P 35/00 |
| 2004/0214825 A1 | 10/2004 | McCall et al. | |
| 2006/0106020 A1 | 5/2006 | Rodgers et al. | |
| 2006/0167047 A1 | 7/2006 | Timmers et al. | |
| 2007/0179165 A1 | 8/2007 | Gyorkos et al. | |
| 2007/0203236 A1 | 8/2007 | Smith et al. | |
| 2007/0254961 A1 | 11/2007 | Tapas et al. | |
| 2009/0326020 A1 | 12/2009 | Yan et al. | |
| 2010/0166781 A1 | 7/2010 | Setiadi et al. | |
| 2010/0179325 A1 | 7/2010 | Suzuki et al. | |
| 2010/0216853 A1 | 8/2010 | Marmorstein et al. | |
| 2010/0267672 A1 | 10/2010 | Jung et al. | |
| 2011/0257196 A1 | 10/2011 | Yan et al. | |
| 2012/0108581 A1 | 5/2012 | Ashikawa et al. | |
| 2012/0258953 A1 | 10/2012 | Aay et al. | |
| 2013/0158003 A1 | 6/2013 | Campbell et al. | |
| 2013/0324580 A1 | 12/2013 | Zhang et al. | |
| 2016/0158207 A1 | 9/2016 | Adler et al. | |
| 2016/0257692 A1 | 9/2016 | Bair et al. | |

FOREIGN PATENT DOCUMENTS

| | | |
|---|---|---|
| EP | 2 412 710 A1 | 1/2012 |
| WO | WO 1995/020589 A1 | 8/1995 |
| WO | WO 2002/040614 A1 | 5/2002 |
| WO | WO 2003/033517 A1 | 4/2003 |
| WO | WO 2003/045929 A1 | 6/2003 |
| WO | WO 2004/043392 A2 | 5/2004 |
| WO | WO 2005/066162 A1 | 7/2005 |
| WO | WO 2007/120339 A1 | 10/2007 |
| WO | WO 2007/133653 A2 | 11/2007 |
| WO | WO 2008/009348 A1 | 1/2008 |
| WO | WO 2009/000413 A1 | 12/2008 |
| WO | WO 2009/064251 A1 | 5/2009 |

(Continued)

OTHER PUBLICATIONS

Venkatesh,, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784).*
Dorwald F. A. Side Reactions in Organic Synthesis, 2005, Wiley: VCH, Weinheim p. IX of Preface p. 1-15.*
West, Solid State Chemistry and Its Applications, john Wiley & Sons, 1984.*
Feldman, Health Affairs Jun. 2022 41:6, 801-804.*
Dwivedi, Technology in Society 32 (2010) 324-330).*
Extended European Search Report from corresponding application EP 19 18 3741 (dated Aug. 1, 2019).
International Search Report from related application PCT/US2018/051235 (dated Feb. 25, 2019).

(Continued)

*Primary Examiner* — Nizal S Chandrakumar
(74) *Attorney, Agent, or Firm* — Polsinelli PC

(57) ABSTRACT

The present disclosure is directed to inhibitors of the CBP/p300 family of bromodomains. The compounds can be useful in the treatment of disease or disorders associated with the inhibition of the CBP/p300 family of bromodomains. For instance, the disclosure is concerned with compounds and compositions for inhibition of the CBP/p300 family of bromodomains, methods of treating, preventing, or ameliorating diseases or disorders associated with the inhibition of CBP/p300 family of bromodomains, and methods of synthesis of these compounds.

19 Claims, 16 Drawing Sheets

(56) References Cited

FOREIGN PATENT DOCUMENTS

| | | |
|---|---|---|
| WO | WO 2009/152072 A1 | 12/2009 |
| WO | WO 2010/118208 A1 | 10/2010 |
| WO | WO 2010/138490 A1 | 12/2010 |
| WO | WO 2011/085039 A2 | 7/2011 |
| WO | WO 2011/109059 A1 | 9/2011 |
| WO | WO 2011/150156 A2 | 12/2011 |
| WO | WO 2012/019093 A1 | 2/2012 |
| WO | WO 2012/080729 A2 | 6/2012 |
| WO | WO 2012/082837 A1 | 6/2012 |
| WO | WO 2012/116135 A1 | 8/2012 |
| WO | WO 2013/004995 A1 | 1/2013 |
| WO | WO 2013/006485 A1 | 1/2013 |
| WO | WO 2013/148114 A1 | 10/2013 |
| WO | WO 2014/045305 A1 | 3/2014 |
| WO | WO 2014/133414 A2 | 9/2014 |
| WO | WO 2014/182929 A1 | 11/2014 |
| WO | WO 2015/002754 A2 | 1/2015 |
| WO | WO 2015/004533 A2 | 1/2015 |
| WO | WO 2015/013635 A2 | 1/2015 |
| WO | WO 2015/022322 A1 | 2/2015 |
| WO | WO 2015/073763 A1 | 5/2015 |
| WO | WO 2015/074064 A2 | 5/2015 |
| WO | WO 2015/074081 A1 | 5/2015 |
| WO | WO 2016/044694 A1 | 3/2016 |
| WO | WO 2016/086200 A1 | 6/2016 |
| WO | WO 2016/110821 A1 | 7/2016 |
| WO | WO 2016/128908 A1 | 8/2016 |
| WO | WO 2016/170323 A1 | 10/2016 |
| WO | WO 2016/170324 A1 | 10/2016 |
| WO | WO 2017/197056 A1 | 11/2017 |
| WO | WO 2017/197240 A1 | 11/2017 |
| WO | WO 2017/205536 A2 | 11/2017 |
| WO | WO 2018/073586 A1 | 4/2018 |
| WO | WO 2018/073587 A1 | 4/2018 |
| WO | WO 2019/055869 A1 | 3/2019 |
| WO | WO 2019/055877 A1 | 3/2019 |

OTHER PUBLICATIONS

International Search Report from related application PCT/US2018/051214 (dated Dec. 4, 2018).
International Search Report from related application PCT/US2017/034320 (dated Nov. 15, 2017)
International Search Report from related application PCT/US2014/066198 (dated May 18, 2015).
International Search Report from related Application No. PCT/US2019/039936 (dated Sep. 23, 2019).
International Search Report from related Application No. PCT/US2020/022783 (dated Jun. 10, 2020).
International Search Report from related Application No. PCT/US2020/022818 (dated Jun. 15, 2020).
International Search Report from related Application No. PCT/US2020/022823 (dated Jun. 15, 2020).
PubChem CID: 138472436, create date, Aug. 20, 2019, p. 2 formula.
PubChem CID 136574372, deposited Jan. 24, 2019, pp. 1-8, p. 2.
"AR: Androgen Receptor", Depmap Portal, https://depmap.org/portal/gene/AR?tab=characterization (release 19Q2).
"Gene Set: Hallmark_Androgen Response", Gene Set Enrichment Analysis, http://software.broadinstitute.org/gsea/msigdb/cards/HALLMARK_ANDROGEN_RESPONSE.html.
Bowers, et al. Virtual Ligand Screening of the p300/CBP Histone Acetyltransferase: Identification of a Selective Small Molecule Inhibitor, Chemistry & Biology 17, pp. 471-482, May 28, 2010.
Chekler, Eugene L. et al. "Transcriptional Profiling of a Selective CREB Binding Protein Bromodomain Inhibitor Highlights Therapeutic Opportunities", Chemistry and Biology, 2015, 22(12), 1588-1596.
Crawford et al. "Discovery of A Potent and Selective Vivo Probe (GNE-272) for the Bromodomains fo CBP/EP300", J. Med. Chem., 2016, 56 pgs.
Duncan, A. Hay et al. "Discovery and Optimization of Small Molecule Ligands for the CBP/p300 Bromodomains", J. Am. Chem. Soc., 2014, 136(26), 9308-9319.
Fan et al. "p300 Modulates the BRCA1 Inhibition of Estrogen Receptor Activity", Cancer Research, 2002, 62, 141-151.
Garcia-Carpizo et al. "CREBBP/EP300 bromodomain inhibition affects the proliferation of AR positive breast cancer cell lines", Molecular Cancer Research, 2019.
Goff, Corinne Le et al. "Synthesis of some novel fused tetracyclic quinolonecarboxylic acids via 7-methyl-6,7,8,9-tetrahydro-3H-imidazo[4,5-f]quinoline and 6-methyl-5,6,7,8-tetrahydro-1H-imidazo[4,5-g]quinoline", Journal of Heterocyclic Chemistry, 1994, 31(1), 153-160.
Jiang et al., "Small molecule Nas-e targeting cAMP response element binding protein (CREB) and CREB-binding protein interaction inhibits breast cancer bone metastasis" Journal of Cellular and Molecular Medicine, Nov. 20, 2018, vol. 23, pp. 1224-1234.
Jin et al. "Therapeutic Targeting of the CBP/p300 Bromodomain Blocks the Growth of Castration-Resistant Prostate Cancer", Cancer Research, 2017, 77(20), 5564-5575.
Kumar et al. "Androgen Receptor Immunohistochemistry as a Companion Diagnostic Approach to Predict Clinical Response to Enzalutamide in Triple-Negative Breast Cancer", JCO Precision Oncology, 2017, DOI: 10.1200/PO.17.00075.
Lasko et al. "Discovery of a selective catalytic p300/CBP inhibitor that targets lineage-specific tumours", Nature, 2017, vol. 000, 17 pgs.
Robinson et al., "Androgen receptor driven transcription in molecular apocrine breast cancer is mediated by FoxA1", The EMBO Journal, 2011, 30, 3019-3027.
Safarpour, Damoun et al. "Androgen receptor (AR) expression in 400 breast carcinomas: is routine AR assessment justified?", Am J Cancer Res, 2014, 4(4), 353-368.
Scher, Howard et al. "Association of AR-V7 on Circulating Tumor Cells as a Treatment-Specific Biomarker With Outcomes and Survival in Castration-Resistant Prostate Cancer", JAMA Oncology, 2016, 2(11), 1441-1449.
Scher et al. "Assessment of the Validity of Nuclear-Localized Androgen Receptor Splice Variant 7 in Circulating Tumor Cells as a Predictive Biomarker for Castration-Resistant Prostate Cancer" JAMA Oncology, 2018, 4(9), 1179-1186.
Snow et al., "Discovery of 2-Phenylamino-imidazo[4,5-h]isoquinolin-9-ones: a New Class of Inhibitors of Lck Kinase", Journal of Medicinal Chemistry, vol. 45, pp. 3394-3405.
Solankee et al. "Synthesis and evaluation of some novel S-triazine based chalcones and their derivatives",Der Pharma Chemica, 2011, 3(6), 317-324.
Traina et al. "Enzalutamide for the Treatment of Androgen Receptor-Expressing Triple-Negative Breast Cancer" Journal of Clinical Oncology, 2018, 36(9), 884-890.
Tucci, Marcello et al. "Enzalutamide-resistant castration-resistant prostate cancer: challenges and solutions", OncoTargets and Therapy, 2018, 11, 7353-7368.
Wong et al. "Anti-tumor activity of targeted and cytotoxic agents in murine subcutaneous tumor models correlates with clinical response", Clinical Cancer Research, 2012.
European Search Report from corresponding application EP 20 77 3477 (dated Nov. 21, 2022).
Moustakim et al.,, "Discovery of a PCAF Bromodomain Chemical Probe", Angewandte chemie, Dec. 14, 2016 , pp. 845-849, vol. 129.
Dhaliwal JS, Rosani A, Saadabadi A. Diazepam. Aug. 28, 2023. In: StatPearls [Internet]. Treasure Island (FL): StatPearls Publishing; Jan. 2024. PMID: 30725707. Available from: https://www.ncbi.nlm.nih.gov/books/NBK537022/?report=printable.
Friedman H, Greenblatt DJ, Peters GR, Metzler CM, Charlton MD, Harmatz JS, Antal EJ, Sanborn EC, Francom SF. Pharmacokinetics and pharmacodynamics of oral diazepam: effect of dose, plasma concentration, and time. Clin Pharmacol Ther. Aug. 1992;52(2):139-50. doi: 10.1038/clpt.1992.123. PMID: 1505149.
Barreiro EJ, Kümmerle AE, Fraga CA. The methylation effect in medicinal chemistry. Chem Rev. Sep. 14, 2011;111(9):5215-46. doi: 10.1021/cr200060g. Epub Jun. 1, 2011. PMID: 21631125.

(56) References Cited

OTHER PUBLICATIONS

Sun S, Fu J. Methyl-containing pharmaceuticals: Methylation in drug design. Bioorg Med Chem Lett. Nov. 1, 2018;28(20):3283-3289. doi: 10.1016/j.bmcl.2018.09.016. Epub Sep. 14, 2018. PMID: 30243589.
Pinheiro PSM, Franco LS, Fraga CAM. The Magic Methyl and Its Tricks in Drug Discovery and Development. Pharmaceuticals (Basel). Aug. 15, 2023;16(8):1157. doi: 10.3390/ph16081157. PMID: 37631072; PMCID: PMC10457765.

\* cited by examiner

| Compound No. | Structure | Name | Eluted Isomer | CBP IC$_{50}$ (μM gmean) | BRD4 IC$_{50}$ (μM gmean) |
|---|---|---|---|---|---|
| 413 | 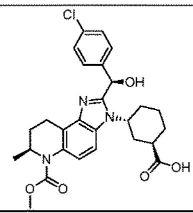 | (1R,3R)-3-((S)-2-((R)-(4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 414 | 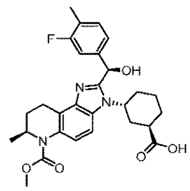 | (1R,3R)-3-((S)-2-((R)-(3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 415 | 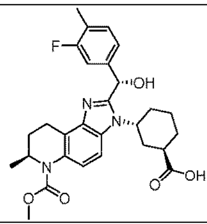 | (1R,3R)-3-((S)-2-((S)-(3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 416 | 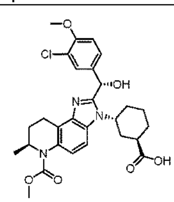 | (1R,3R)-3-((S)-2-((S)-(3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 417 | 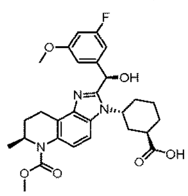 | (1R,3R)-3-((S)-2-((R)-(3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 418 | 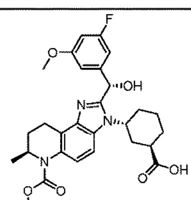 | (1R,3R)-3-((S)-2-((S)-(3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |

Figure 1

| Compound No. | Structure | Name | Eluted Isomer | CBP IC$_{50}$ (µM gmean) | BRD4 IC$_{50}$ (µM gmean) |
|---|---|---|---|---|---|
| 419 | 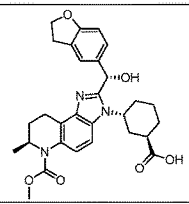 | (1R,3R)-3-((S)-2-((S)-(2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 420 | 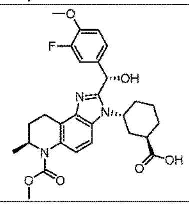 | (1R,3R)-3-((S)-2-((S)-(3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 421 | 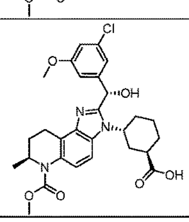 | (1R,3R)-3-((S)-2-((S)-(3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 423 | 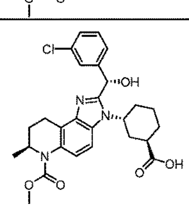 | (1R,3R)-3-((S)-2-((S)-(3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 424 | 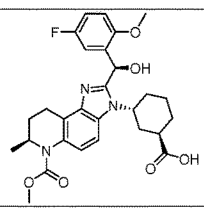 | (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 426 | 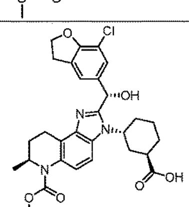 | (1R,3R)-3-((S)-2-((S)-(7-chloro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 427 | 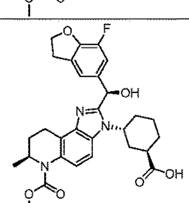 | (1R,3R)-3-((S)-2-((R)-(7-fluoro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1st | ++++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 428 | 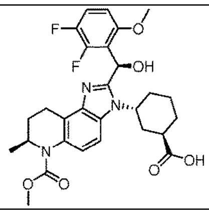 | (1R,3R)-3-((S)-2-((R)-(2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 429 | 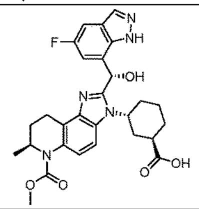 | (1R,3R)-3-((S)-2-((S)-(5-fluoro-1H-indazol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 430 | 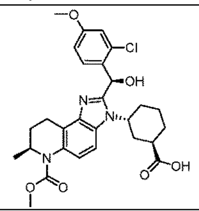 | (1R,3R)-3-((S)-2-((R)-(2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 431 | 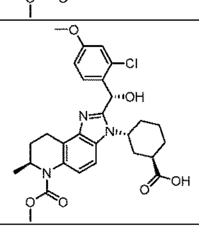 | (1R,3R)-3-((S)-2-((S)-(2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 432 | 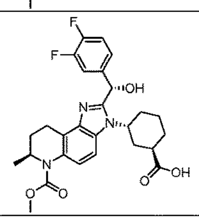 | (1R,3R)-3-((S)-2-((S)-(3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 433 | 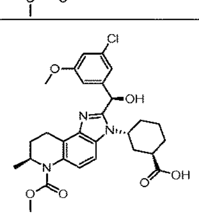 | (1R,3R)-3-((S)-2-((R)-(3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 434 | 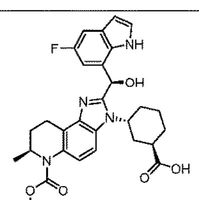 | (1R,3R)-3-((S)-2-((R)-(5-fluoro-1H-indol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 436 | 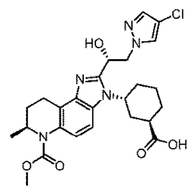 | (1R,3R)-3-((S)-2-((R)-2-(4-chloro-1H-pyrazol-1-yl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 437 | 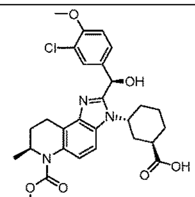 | (1R,3R)-3-((S)-2-((R)-(3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 438 | 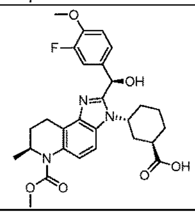 | (1R,3R)-3-((S)-2-((R)-(3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 440 | 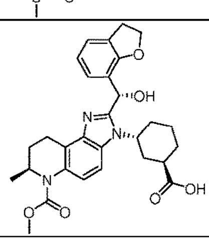 | (1R,3R)-3-((S)-2-((S)-(2,3-dihydrobenzofuran-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 442 | 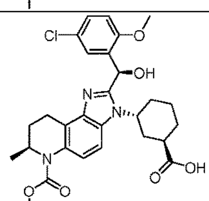 | (1R,3R)-3-((S)-2-((R)-(5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 444 | 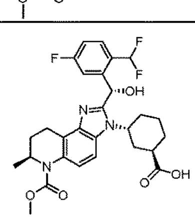 | (1R,3R)-3-((S)-2-((S)-(2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 445 | 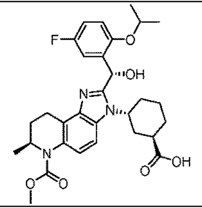 | (1R,3R)-3-((S)-2-((S)-(5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 448 | 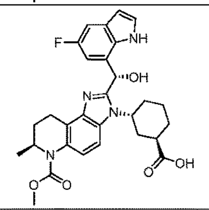 | (1R,3R)-3-((S)-2-((S)-(5-fluoro-1H-indol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 449 | 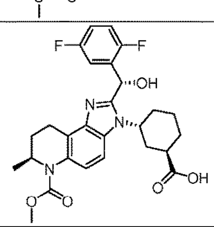 | (1R,3R)-3-((S)-2-((S)-(2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | + |
| 451 | 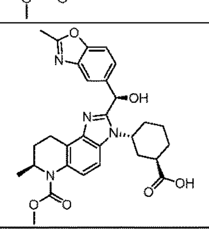 | (1R,3R)-3-((S)-2-((R)-hydroxy(2-methylbenzo[d]oxazol-5-yl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 452 | 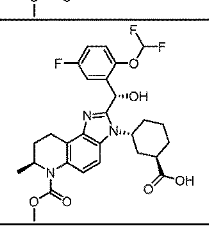 | (1R,3R)-3-((S)-2-((S)-(2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | | ++++ | ++ |
| 453 | 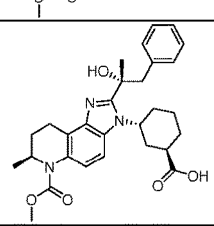 | (1R,3R)-3-((S)-2-((R)-2-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | +++ |
| 454 | 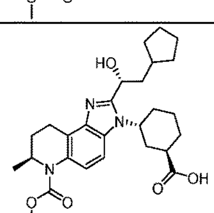 | (1R,3R)-3-((S)-2-((R)-2-cyclopentyl-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 458 | 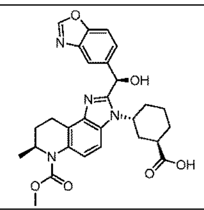 | (1R,3R)-3-((S)-2-((R)-benzo[d]oxazol-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 460 | 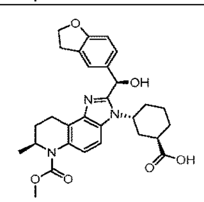 | (1R,3R)-3-((S)-2-((R)-(2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 461 | 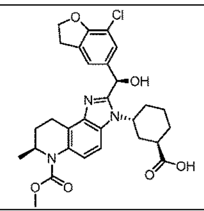 | (1R,3R)-3-((S)-2-((R)-(7-chloro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 462 | 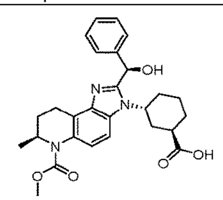 | (1R,3R)-3-((S)-2-((R)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 464 | 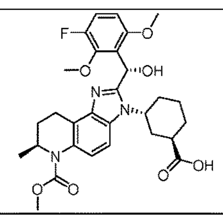 | (1R,3R)-3-((S)-2-((S)-(3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 467 | 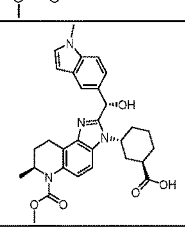 | (1R,3R)-3-((S)-2-((S)-hydroxy(1-methyl-1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 470 | 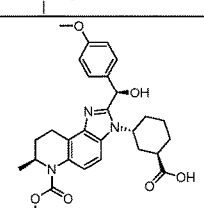 | (1R,3R)-3-((S)-2-((R)-hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |

Figure 1 (Continued)

| Compound No. | Structure | Name | Eluted Isomer | CBP IC$_{50}$ (µM gmean) | BRD4 IC$_{50}$ (µM gmean) |
|---|---|---|---|---|---|
| 472 | 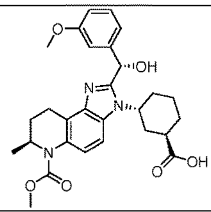 | (1R,3R)-3-((S)-2-((S)-hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 474 | 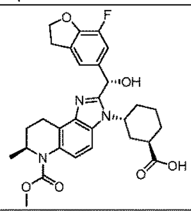 | (1R,3R)-3-((S)-2-((S)-(7-fluoro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 478 | 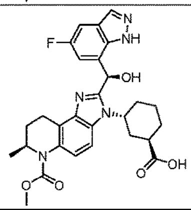 | (1R,3R)-3-((S)-2-((R)-(5-fluoro-1H-indazol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 479 | 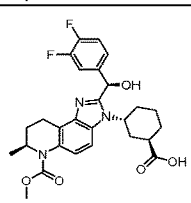 | (1R,3R)-3-((S)-2-((R)-(3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 480 | 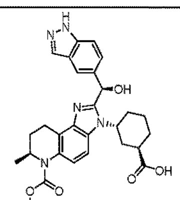 | (1R,3R)-3-((S)-2-((R)-hydroxy(1H-indazol-5-yl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |
| 482 | 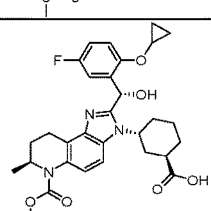 | (1R,3R)-3-((S)-2-((S)-(2-cyclopropoxy-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 488 | 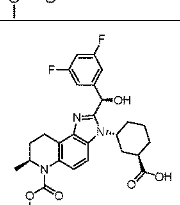 | (1R,3R)-3-((S)-2-((R)-(3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 491 | 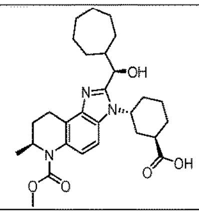 | (1R,3R)-3-((S)-2-((R)-cycloheptyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1st | ++++ | ++ |
| 493 | 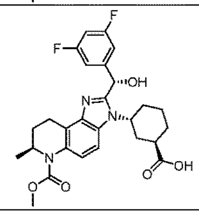 | (1R,3R)-3-((S)-2-((S)-(3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2nd | ++++ | ++ |
| 499 | 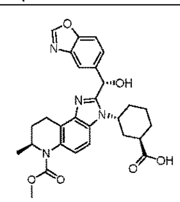 | (1R,3R)-3-((S)-2-((S)-benzo[d]oxazol-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2nd | ++++ | ++ |
| 501 | 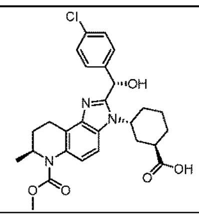 | (1R,3R)-3-((S)-2-((S)-(4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2nd | ++++ | ++ |
| 503 | 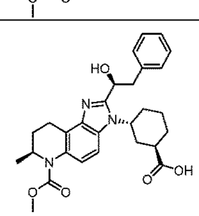 | (1R,3R)-3-((S)-2-((S)-1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid | 2nd | ++++ | ++ |
| 515 | 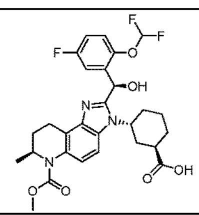 | (1R,3R)-3-((S)-2-((R)-(2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | | ++++ | + |
| 523 | 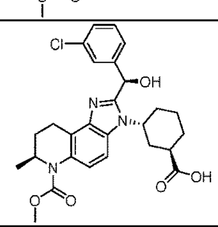 | (1R,3R)-3-((S)-2-((R)-(3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1st | ++++ | ++ |

Figure 1 (Continued)

| Compound No. | Structure | Name | Eluted Isomer | CBP IC$_{50}$ (µM gmean) | BRD4 IC$_{50}$ (µM gmean) |
|---|---|---|---|---|---|
| 528 | 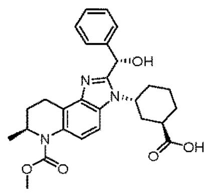 | (1R,3R)-3-((S)-2-((S)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | | ++++ | ++ |
| 534 | 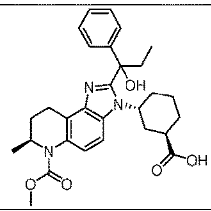 | (1R,3R)-3-((7S)-2-(1-hydroxy-1-phenylpropyl)-6-(methoxycarbonyl)-7-methyl-6,7,8,9-tetrahydro-3H-imidazo[4,5-f]quinolin-3-yl)cyclohexane-1-carboxylic acid | | ++++ | + |
| 537 | 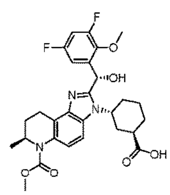 | (1R,3R)-3-((S)-2-((S)-(3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 538 | 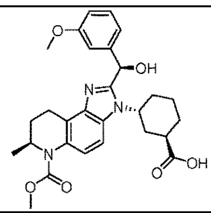 | (1R,3R)-3-((S)-2-((R)-hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 542 | 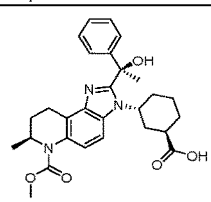 | (1R,3R)-3-((S)-2-((R)-1-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 564 | 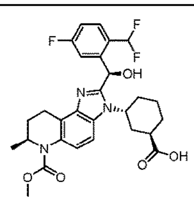 | (1R,3R)-3-((S)-2-((R)-(2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 565 | 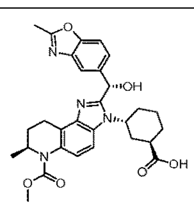 | (1R,3R)-3-((S)-2-((S)-hydroxy(2-methylbenzo[d]oxazol-5-yl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | + |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 566 | 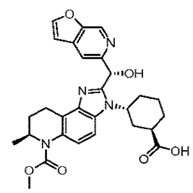 | (1R,3R)-3-((S)-2-((S)-furo[2,3-c]pyridin-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 569 | 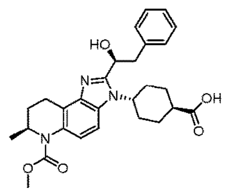 | (1S,4r)-4-((S)-2-((S)-1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 572 | 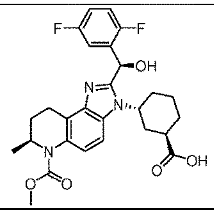 | (1R,3R)-3-((S)-2-((R)-(2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 578 | 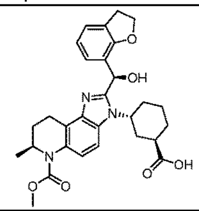 | (1R,3R)-3-((S)-2-((R)-(2,3-dihydrobenzofuran-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 587 | 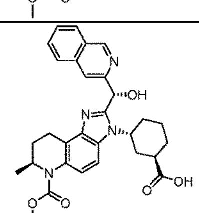 | (1R,3R)-3-((S)-2-((S)-hydroxy(isoquinolin-3-yl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | ++ |
| 589 | 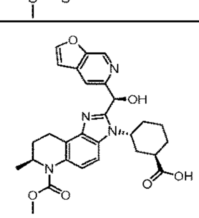 | (1R,3R)-3-((S)-2-((R)-furo[2,3-c]pyridin-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | ++++ | + |
| 596 | 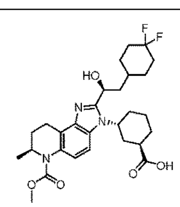 | (1R,3R)-3-((S)-2-((S)-2-(4,4-difluorocyclohexyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | ++++ | + |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 606 | 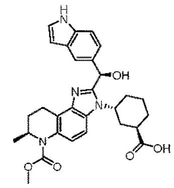 | (1R,3R)-3-((S)-2-((R)-hydroxy(1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | +++ |
| 607 | 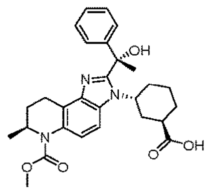 | (1R,3R)-3-((S)-2-((S)-1-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 608 | 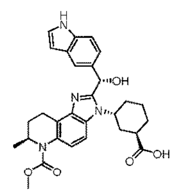 | (1R,3R)-3-((S)-2-((S)-hydroxy(1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | +++ |
| 610 | 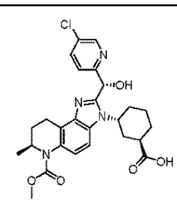 | (1R,3R)-3-((S)-2-((S)-(5-chloropyridin-2-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 612 | 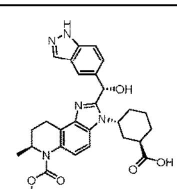 | (1R,3R)-3-((S)-2-((S)-hydroxy(1H-indazol-5-yl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | ++ |
| 615 | 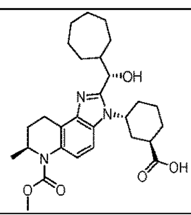 | (1R,3R)-3-((S)-2-((S)-cycloheptyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 618 | 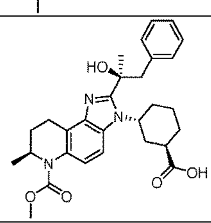 | (1R,3R)-3-((S)-2-((S)-2-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 625 | 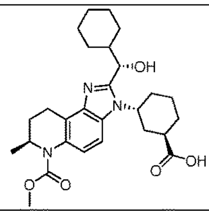 | (1R,3R)-3-((S)-2-((S)-cyclohexyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 630 | 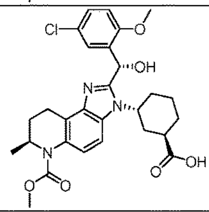 | (1R,3R)-3-((S)-2-((S)-(5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | ++ |
| 631 | 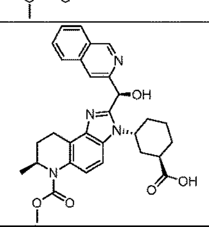 | (1R,3R)-3-((S)-2-((R)-hydroxy(isoquinolin-3-yl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 636 | 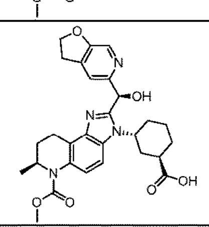 | (1R,3R)-3-((S)-2-((R)-(2,3-dihydrofuro[2,3-c]pyridin-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 637 | 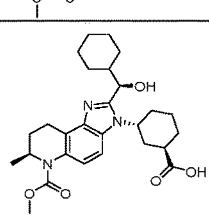 | (1R,3R)-3-((S)-2-((R)-cyclohexyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 638 | 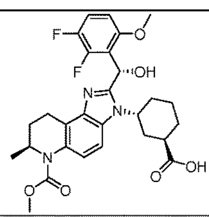 | (1R,3R)-3-((S)-2-((S)-(2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 649 | 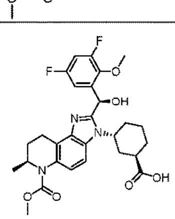 | (1R,3R)-3-((S)-2-((R)-(3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 654 | 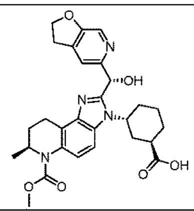 | (1R,3R)-3-((S)-2-((S)-(2,3-dihydrofuro[2,3-c]pyridin-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 660 | 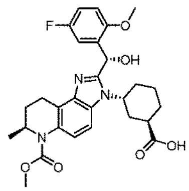 | (1R,3R)-3-((S)-2-((S)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 662 | 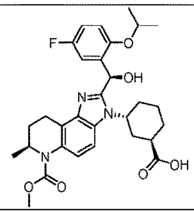 | (1R,3R)-3-((S)-2-((R)-(5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | ++ |
| 674 | 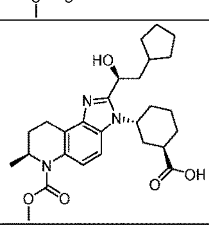 | (1R,3R)-3-((S)-2-((S)-2-cyclopentyl-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 678 | 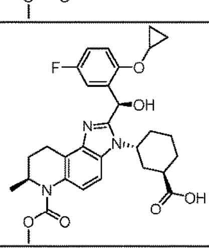 | (1R,3R)-3-((S)-2-((R)-(2-cyclopropoxy-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | ++ |
| 682 | 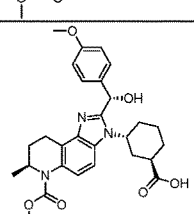 | (1R,3R)-3-((S)-2-((S)-hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 699 | 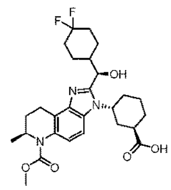 | (1R,3R)-3-((S)-2-((R)-(4,4-difluorocyclohexyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 701 | 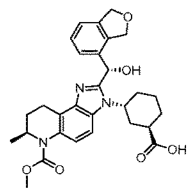 | (1R,3R)-3-((S)-2-((S)-(1,3-dihydroisobenzofuran-4-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 708 | 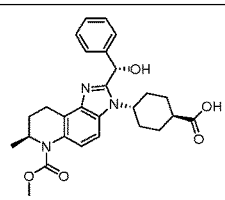 | (1S,4r)-4-((S)-2-((S)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 712 | 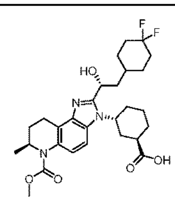 | (1R,3R)-3-((S)-2-((R)-2-(4,4-difluorocyclohexyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 730 | 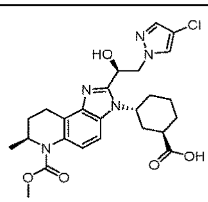 | (1R,3R)-3-((S)-2-((S)-2-(4-chloro-1H-pyrazol-1-yl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 731 | 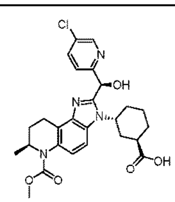 | (1R,3R)-3-((S)-2-((R)-(5-chloropyridin-2-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 735 | 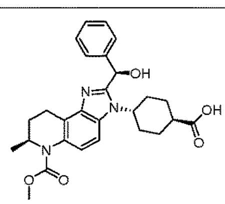 | (1R,4r)-4-((S)-2-((R)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 747 | 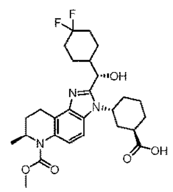 | (1R,3R)-3-((S)-2-((S)-(4,4-difluorocyclohexyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 749 | 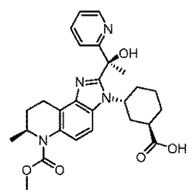 | (1R,3R)-3-((S)-2-((R)-1-hydroxy-1-(pyridin-2-yl)ethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 762 | 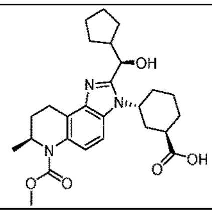 | (1R,3R)-3-((S)-2-((R)-cyclopentyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 770 | 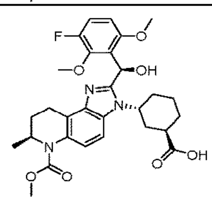 | (1R,3R)-3-((S)-2-((R)-(3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 774 | 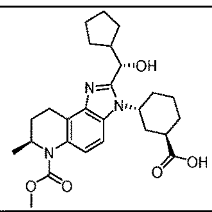 | (1R,3R)-3-((S)-2-((S)-cyclopentyl(hydroxy)methyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 781 | 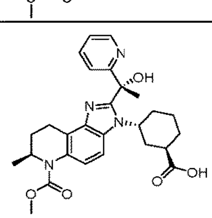 | (1R,3R)-3-((S)-2-((S)-1-hydroxy-1-(pyridin-2-yl)ethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | +++ | + |
| 817 | 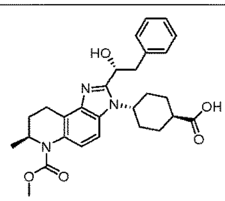 | (1R,4r)-4-((S)-2-((R)-1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | ++ |

Figure 1 (Continued)

| Compound No. | Structure | Name | Eluted Isomer | CBP IC$_{50}$ (μM gmean) | BRD4 IC$_{50}$ (μM gmean) |
|---|---|---|---|---|---|
| 822 | 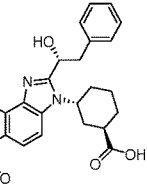 | (1R,3R)-3-((S)-2-((R)-1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | + |
| 826 | 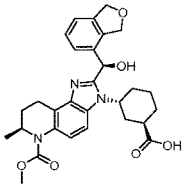 | (1R,3R)-3-((S)-2-((R)-(1,3-dihydroisobenzofuran-4-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | +++ | ++ |
| 957 | 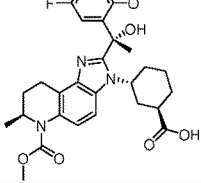 | (1R,3R)-3-((S)-2-((S)-1-(5-fluoro-2-methoxyphenyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 2$^{nd}$ | + | + |
| 960 | 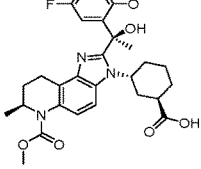 | (1R,3R)-3-((S)-2-((R)-1-(5-fluoro-2-methoxyphenyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | + | + |
| 962 | 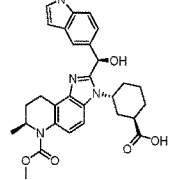 | (1R,3R)-3-((S)-2-((R)-hydroxy(1-methyl-1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | 1$^{st}$ | + | +++ |

Figure 1 (Continued)

INHIBITING CREB BINDING PROTEIN (CBP)

CROSS-REFERENCE TO RELATED APPLICATIONS

This application is a continuation of U.S. patent application Ser. No. 16/946,159, filed Jun. 8, 2020, which is a continuation of Ser. No. 16/457,596, filed Jun. 28, 2019, which claims the benefit of U.S. Provisional Application No. 62/692,593, filed Jun. 29, 2018, and U.S. Provisional Application No. 62/819,490, filed Mar. 15, 2019, and the benefit of foreign priority under 35 U.S.C. § 365(a) to International Application No. PCT/US2018/051235, filed Sep. 14, 2018, and International Application No. PCT/US2018/051214, filed Sep. 14, 2018, each of which is incorporated by reference in its entirety.

TECHNICAL FIELD

This disclosure relates to novel chemical compositions for inhibiting the CREB binding protein (CBP), useful in the treatment of diseases or disorders associated with the inhibition of CBP/p300 family of bromodomains.

BACKGROUND

CBP/p300 are lysine acetyltransferases that catalyze the attachment of an acetyl group to a lysine side chain of histones and other protein substrates. p300 (also known as EP300 and KAT3B) is a protein with multiple domains that bind to diverse proteins including many DNA binding transcription factors. The cyclic AMP-responsive element-binding protein (CREB) binding protein (CBP, also known as KAT3A) is a cellular paralog of p300. p300 and CBP share extensive sequence identity and functional similarity and are often referred to as CBP/p300. CBP/p300-catalyzed acetylation of histones and other proteins is pivotal to gene activation. Heightened p300 expression and activities have been observed in advanced human cancers such as prostate and in human primary breast cancer specimens. Chemical inhibition of CBP/p300 that possesses intrinsic acetyltransferase enzymatic activity is more feasible than blocking transcription factors with small molecules, as discovery of chemical inhibitors of transcription factors has proven extremely challenging. Accordingly, there is a need for novel and potent compounds for inhibiting CBP/p300, useful as therapies for treating certain related forms of cancer.

SUMMARY

A first aspect of the present disclosure relates to compounds of Formula (I):

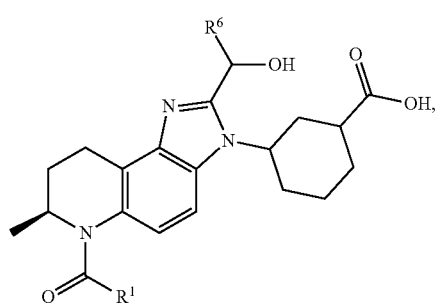

(I)

or a pharmaceutically acceptable salt, enantiomer, hydrate, solvate, isomer, or tautomer thereof, wherein:

$R^1$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —$OR^5$, —$N(R^5)_2$, or —$NHR^5$;

$R^5$ is —$C_1$-$C_6$ alkyl, —$C_3$-$C_8$ cycloalkyl, heterocyclyl, aryl, or heteroaryl;

$R^6$ is —$C_1$-$C_6$ alkyl, —$C_3$-$C_8$ cycloalkyl, —$C_4$-$C_8$ cycloalkenyl, heterocyclyl, aryl, spirocycloalkyl, spiroheterocyclyl, heteroaryl, halogen, oxo, —$(CH_2)_n$—$OR^8$, —$C(O)R^{8'}$, —$C(O)OR^8$, or —$C(O)NR^8R^9$, wherein each alkyl, cycloalkyl, heterocyclyl, spirocycloalkyl, spiroheterocyclyl, heteroaryl, or aryl is optionally substituted with one or more $R^{10}$;

$R^8$ and $R^9$ are each independently, at each occurrence, —H, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a spiroheterocyclyl, heterocyclyl, or heteroaryl, wherein the formed spiroheterocyclyl, heterocyclyl, or heteroaryl is optionally substituted with one or more $R^{10}$ or $R^{11}$;

$R^{8'}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^{10}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$OC_3$-$C_6$ cycloalkyl, —Oaryl, —Oheteroaryl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$.

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl; and $R^{12}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl)$S(O)(C_1$-$C_6$ alkyl).

Preferably, the compounds of Formula (I) are a compound of Formula (IV):

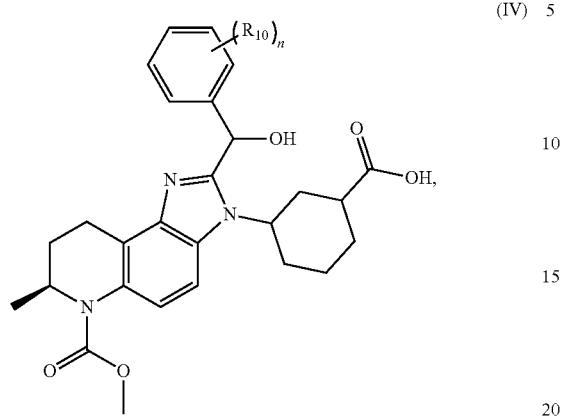

(IV)

or a pharmaceutically acceptable salt thereof, wherein:
n is 0, 1, 2, 3, 4, or 5;
each $R^{10}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$OC_3$-$C_6$ cycloalkyl, —Oaryl, —Oheteroaryl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$.
wherein any two $R^{10}$ when on non-adjacent atoms, can combine to form a bridging cycloalkyl or heterocyclyl;
wherein any two $R^{10}$ when on adjacent atoms, can combine to form a cycloalkyl, heterocyclyl, aryl or heteroaryl; and
$R^{12}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl)$S(O)(C_1$-$C_6$ alkyl).

BRIEF DESCRIPTION OF THE DRAWINGS

FIG. 1 is a table of compounds in accordance with various embodiments of the disclosure.

DETAILED DESCRIPTION

The present disclosure relates to CBP Inhibitor Compounds, defined herein as compounds having one or more of the following characteristics when tested according to the HTRF biochemical Assay Protocol below in Example 5: (1) a CBP $IC_{50}$ value of less than 1 μM; and (2) a CBP $IC_{50}$ value of between 0.001 and 1 μM.

Compounds of the Disclosure

One aspect of the present disclosure describes compounds of Formula (I):

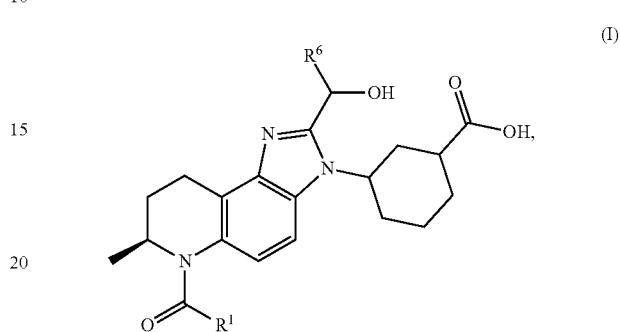

(I)

and pharmaceutically acceptable salts, enantiomers, hydrates, solvates, prodrugs, isomers, and tautomers thereof, wherein $R^1$ and $R^6$ are described above.

In some examples, the compound of Formula (I) is a stereoisomer or enantiomer of Formula (I) selected from the group consisting of Formula (I-a), (I-b), (I-c), (I-d), (I-e), (I-f), (I-g), (I-h), (I-i), (I-j), (I-k), (I-l), (I-m), (I-n), (I-o) and (I-p):

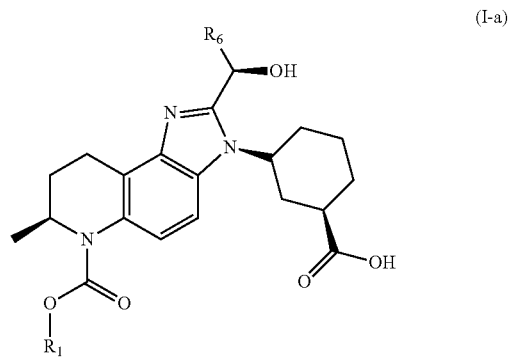

(I-a)

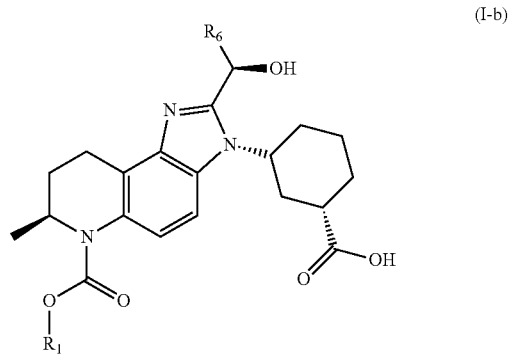

(I-b)

(I-c)
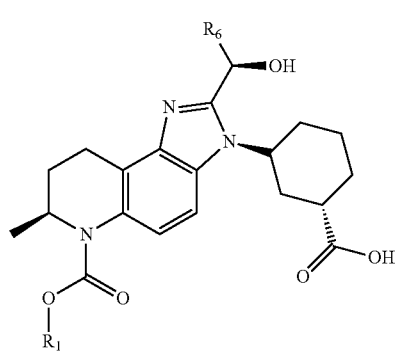
(I-d)
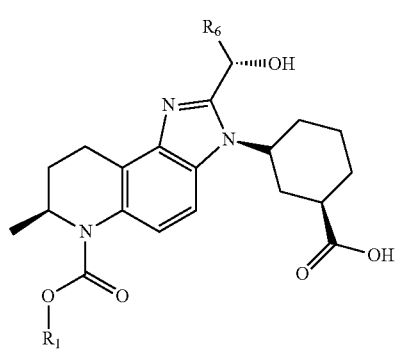
(I-e)
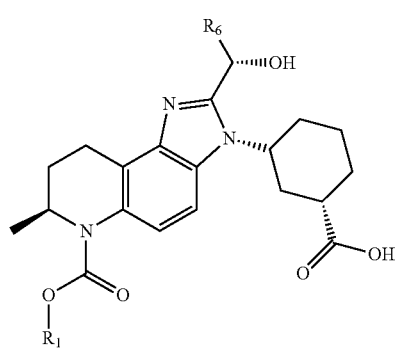
(I-f)
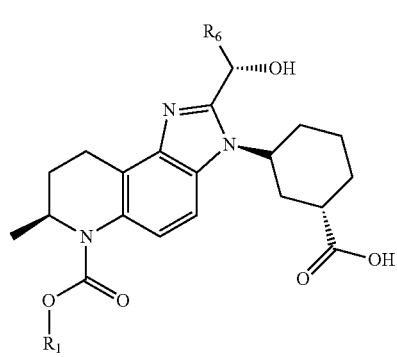
(I-g)
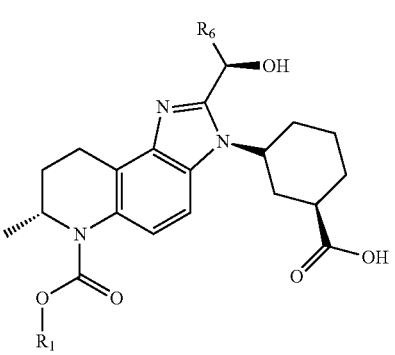
(I-h)
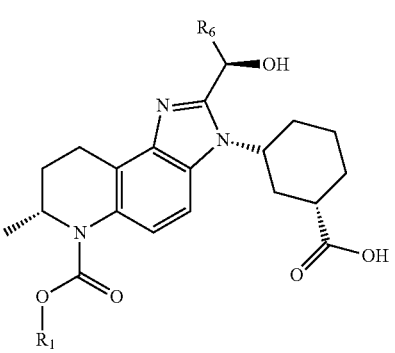
(I-i)
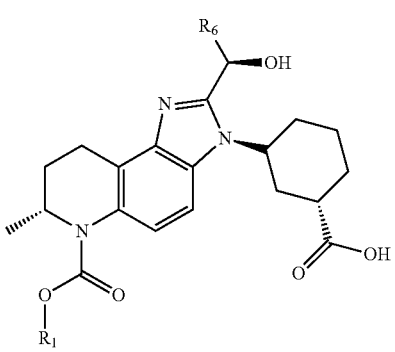
(I-j)
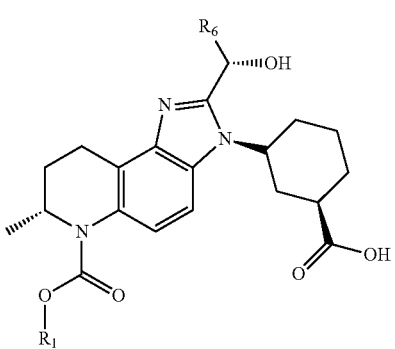

(I-k)

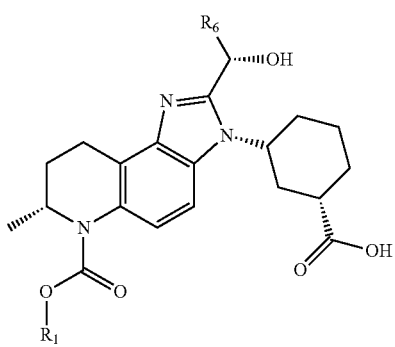

(I-l)

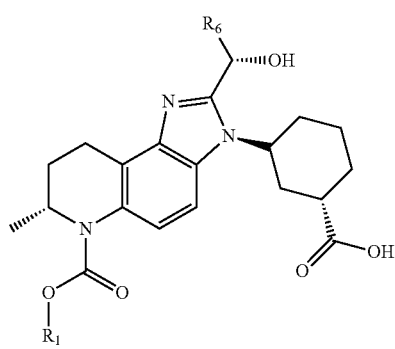

(I-m)

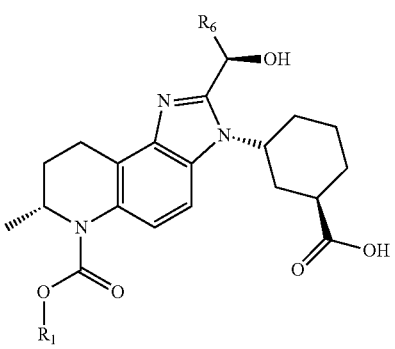

(I-n)

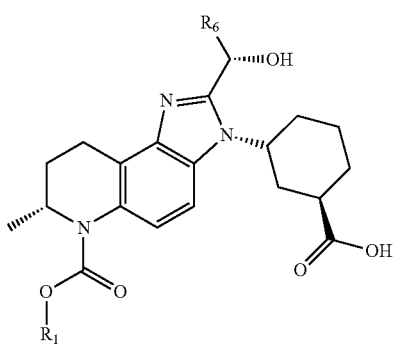

(I-o)

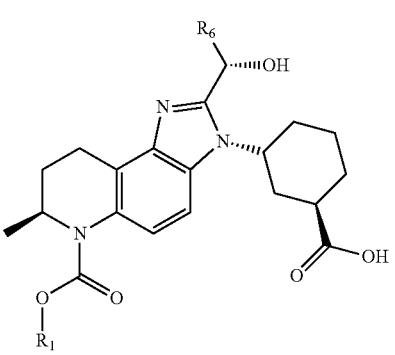

(I-p)

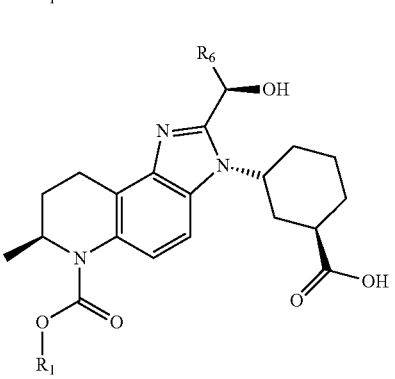

A compound of Formula (I) can be a stereoisomer thereof (e.g., a compound of Formula (I-a), (I-b), (I-c), (I-d), (I-e), (I-f), (I-g), (I-h), (I-i), (I-j), (I-k), (I-l), (I-m), (I-n), (I-o) wherein $R_1$ is methyl and $R_6$ is phenyl optionally substituted with one or more $R^{10}$).

In some preferred embodiments, the compound of Formula (I) is a compound of Formula (IV), including stereoisomers thereof:

(IV)

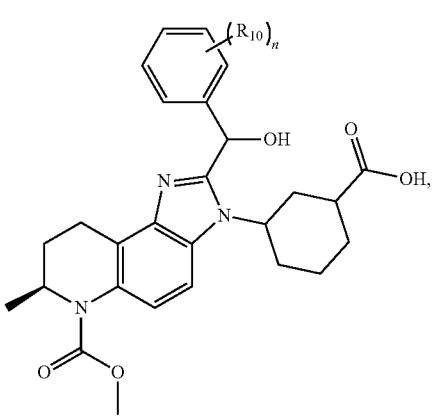

or a pharmaceutically acceptable salt thereof, wherein n is an integer of 0, 1, 2, 3, 4, or 5 (preferably, 0, 1 or 2) and $R_{10}$ is as defined above. Preferably, the compound of Formula (IV) is a compound of Formula (IV-a) (including, for example, compounds of Formula (IV-b), Formula (IV-c) or mixtures thereof), or pharmaceutically acceptable salts thereof, wherein n is an integer of 0, 1, 2, 3, 4 or 5 (preferably 0, 1 or 2) and $R_{10}$ is as defined above.

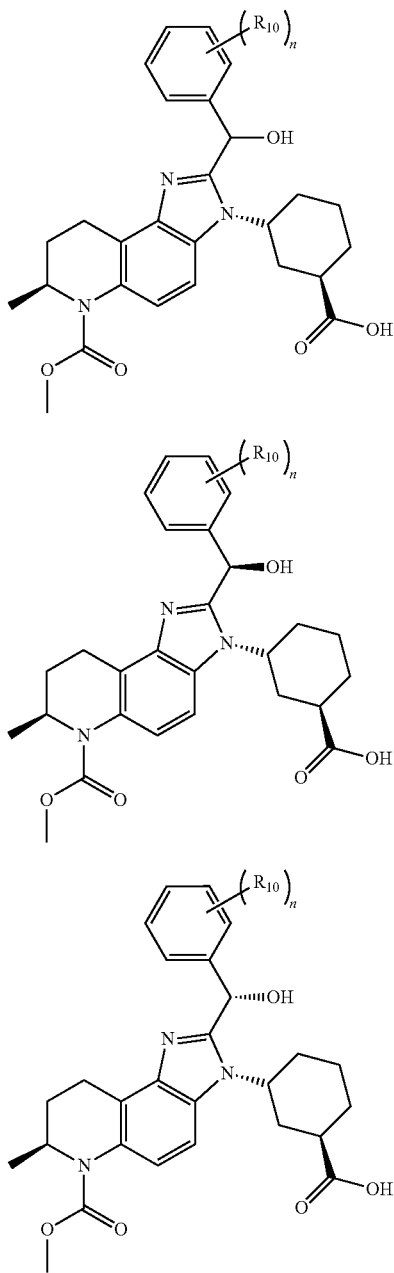

(IV-a)

(IV-b)

(IV-c)

In certain preferred compounds of Formula (IV-a) including compounds of Formula (IV-b) and compounds of Formula (IV-c) wherein n is 0, 1, 2, 3, 4 or 5 and each $R_{10}$ is independently halogen or —$OC_1$-$C_6$ alkyl, and wherein the —$OC_1$-$C_6$ alkyl is optionally substituted with one or more halogen. For example, in certain compounds of Formula (IV-a), n is 0, 1 or 2 and each $R_{10}$ is independently halogen, or —$OC_1$ alkyl optionally substituted with one or more halogen (e.g., fluorine or chlorine). In some compounds of Formula (IV-a), n is 2 and each $R_{10}$ is independently halogen (e.g., fluorine or chlorine), $OC_1$ alkyl substituted with 1, 2 or 3 halogen (e.g., fluorine or chlorine), or methoxy.

Another aspect of the present disclosure is the provision of pharmaceutical compositions comprising therapeutically effective amounts of at least one compound of Formula (I). An aspect of the present disclosure concerns compounds which are, or can be, inhibitors of one or more bromodomains of the CBP/p300 family (e.g., compounds of Formula (I)).

In some embodiments, compounds of the disclosure have the Formula (I)

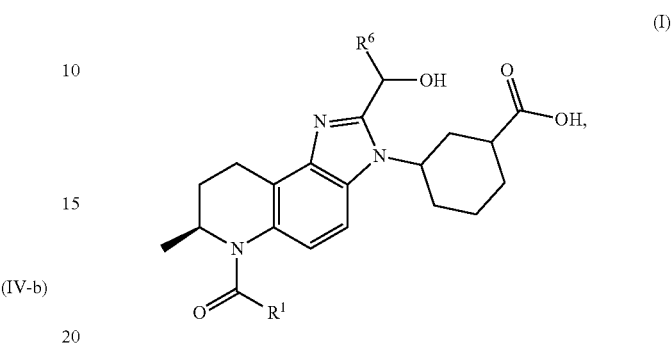

(I)

or a pharmaceutically acceptable salt, enantiomer, hydrate, solvate, isomer, or tautomer thereof, wherein:

$R^1$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —$OR^5$, —$N(R^5)_2$, or —$NHR^5$;

$R^5$ is —$C_1$-$C_6$ alkyl, —$C_3$-$C_8$ cycloalkyl, heterocyclyl, aryl, or heteroaryl;

$R^6$ is —$C_1$-$C_6$ alkyl, —$C_3$-$C_8$ cycloalkyl, —$C_4$-$C_8$ cycloalkenyl, heterocyclyl, aryl, spirocycloalkyl, spiroheterocyclyl, heteroaryl, halogen, oxo, —$(CH_2)_n$—$OR^8$, —$C(O)R^{8'}$, —$C(O)OR^8$, or —$C(O)NR^8R^9$, wherein each alkyl, cycloalkyl, heterocyclyl, spirocycloalkyl, spiroheterocyclyl, heteroaryl, or aryl is optionally substituted with one or more $R^{10}$;

$R^8$ and $R^9$ are each independently, at each occurrence, —H, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a spiroheterocyclyl, heterocyclyl, or heteroaryl, wherein the formed spiroheterocyclyl, heterocyclyl, or heteroaryl is optionally substituted with one or more $R^{10}$ or $R^{11}$;

$R^{8'}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^{10}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$OC_3$-$C_6$ cycloalkyl, —Oaryl, —Oheteroaryl, —$NHC_1$-$C_6$ alkyl, —$N(C_1$-$C_6$ alkyl)$_2$, —$S(O)_2NH(C_1$-$C_6$ alkyl), —$S(O)_2N(C_1$-$C_6$ alkyl)$_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl)$_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl; and $R^{12}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl$)SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl$)S(O)(C_1$-$C_6$ alkyl).

In some embodiments, compounds of the disclosure have the Formula (I)

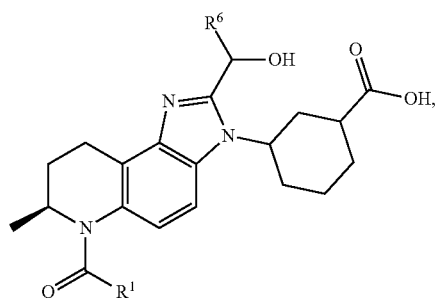

(I)

or a pharmaceutically acceptable salt, enantiomer, hydrate, solvate, isomer, or tautomer thereof, wherein:

$R^1$ is —$OR^5$;

$R^5$ is —$C_1$-$C_6$ alkyl;

$R^6$ is phenyl optionally substituted with one or more $R^{10}$;

$R^{10}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, —$NO_2$, —CN, —$NH_2$, —$OC_1$-$C_6$ alkyl, —$OC_3$-$C_6$ cycloalkyl, —Oaryl, —Oheteroaryl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl$)SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl$)S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl; and $R^{12}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OC_1$-$C_6$ alkyl, —$N(C_1$-$C_6$ alkyl$)SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl$)S(O)(C_1$-$C_6$ alkyl).

In some embodiments, compounds of the disclosure have the Formula (I)

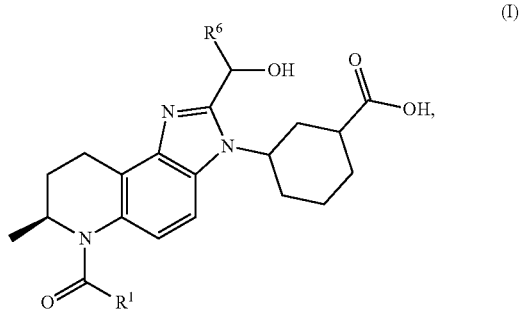

(I)

or a pharmaceutically acceptable salt, enantiomer, hydrate, solvate, isomer, or tautomer thereof, wherein:

$R^1$ is —$OR^5$;

$R^5$ is —$C_1$-$C_3$ alkyl;

$R^6$ is phenyl optionally substituted with one or more $R^{10}$;

$R^{10}$ is each independently, at each occurrence halogen, —$OC_1$-$C_6$ alkyl, —$OC_3$-$C_6$ cycloalkyl, —Oaryl, or —Oheteroaryl, wherein each alkyl, cycloalkyl, aryl or heteroaryl is optionally substituted with one or more —$R^{12}$.

$R^{12}$ is halogen.

In some embodiments, compounds of the disclosure have the Formula (III):

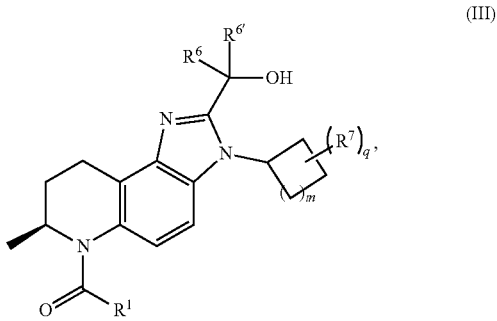

(III)

or a pharmaceutically acceptable salt thereof, wherein, $R^1$ is —$OR^5$;

$R^5$ is —$C_1$-$C_6$ alkyl, —$C_3$-$C_8$ cycloalkyl, heterocyclyl, aryl, or heteroaryl;

$R^6$ is —$C_3$-$C_8$ cycloalkyl, —$C_4$-$C_8$ cycloalkenyl, heterocyclyl, heteroaryl, aryl, wherein each cycloalkyl, cycloalkenyl, heterocyclyl, heteroaryl, or aryl is optionally substituted with one or more —$R^{10}$;

$R^{6'}$ is —H or —$C_1$-$C_6$ alkyl;

$R^7$ is —H, halogen, —OH, —CN, —$OC_1$-$C_6$ alkyl, —$NH_2$, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$S(O)_2OH$, —$C(O)C_1$-$C_6$ alkyl, —$C(O)NH_2$, —$C(O)NH(C_1$-$C_6$ alkyl), —$C(O)N(C_1$-$C_6$ alkyl$)_2$, —$C(O)OH$, —$C(O)OC_1$-$C_6$ alkyl, —$N(C_1$-$C_6$ alkyl)SO$_2$C$_1$-C$_6$ alkyl, —S(O)(C$_1$-C$_6$ alkyl), —S(O)N(C$_1$-C$_6$ alkyl)$_2$, —S(O)$_2$NH$_2$, —N(C$_1$-C$_6$ alkyl)S(O)(C$_1$-C$_6$ alkyl) or tetrazole;

R$^{10}$ is independently, at each occurrence, —C$_1$-C$_6$ alkyl, —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, aryl, —OH, halogen, oxo, —NO$_2$, —CN, —NH$_2$, —OC$_1$-C$_6$ alkyl, —OC$_3$-C$_6$ cycloalkyl, —Oaryl, —Oheteroaryl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —NHC(O)C$_1$-C$_6$ alkyl, —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, or —N(C$_1$-C$_6$ alkyl)S(O)(C$_1$-C$_6$ alkyl), wherein each alkyl, alkenyl, alkynyl, cycloalkyl, cycloalkenyl, heterocyclyl, heteroaryl, or aryl is optionally substituted with one or more —R$^{12}$.

R$^{12}$ is independently, at each occurrence, —C$_1$-C$_6$ alkyl, —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, aryl, —OH, halogen, oxo, —NO$_2$, —CN, —NH$_2$, —OC$_1$-C$_6$ alkyl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, or —N(C$_1$-C$_6$ alkyl)S(O)(C$_1$-C$_6$ alkyl);

m is an integer from 0 to 5; and q is an integer from 0 to 4.

Multiple embodiments of the compounds of Formula (III) are provided herein. In some embodiments R$^{12}$ is halogen. In some embodiments m is 3. In some embodiments R$^{6'}$ is H. In some embodiments R$^6$ is aryl. In some embodiments R$^7$ is —C(O)OH. In some embodiments R$^5$ is methyl.

In some embodiments, compounds of the disclosure have the Formula (I):

(I)

or a pharmaceutically acceptable salt thereof, wherein:

R$^1$ is —OR$^5$;

R$^5$ is —C$_1$-C$_6$ alkyl; and

R$^6$ is phenyl optionally substituted with one or more R$^{10}$;

R$^{10}$ is independently, at each occurrence, —C$_1$-C$_6$ alkyl, —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, aryl, —OH, halogen, —NO$_2$, —CN, —NH$_2$, —OC$_1$-C$_6$ alkyl, —OC$_3$-C$_6$ cycloalkyl, —Oaryl, —Oheteroaryl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —NHC(O)C$_1$-C$_6$ alkyl, —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, or —N(C$_1$-C$_6$ alkyl)S(O)(C$_1$-C$_6$ alkyl), wherein each alkyl, alkenyl, alkynyl, cycloalkyl, cycloalkenyl, heterocyclyl, heteroaryl, or aryl is optionally substituted with one or more —R$^{12}$; and R$^{12}$ is independently, at each occurrence, —C$_1$-C$_6$ alkyl, —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, aryl, —OH, halogen, oxo, —NO$_2$, —CN, —NH$_2$, —OC$_1$-C$_6$ alkyl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, or —N(C$_1$-C$_6$ alkyl)S(O)(C$_1$-C$_6$ alkyl).

In some embodiments, compounds of the disclosure have the Formula (I):

(I)

or a pharmaceutically acceptable salt thereof, wherein:

R$^1$ is —OR$^5$;

R$^5$ is —C$_1$-C$_3$ alkyl;

R$^6$ is phenyl optionally substituted with one or more R$^{10}$;

R$^{10}$ is independently, at each occurrence halogen, —OC$_1$-C$_6$ alkyl, —OC$_3$-C$_6$ cycloalkyl, —Oaryl, or —Oheteroaryl, wherein each alkyl, cycloalkyl, aryl or heteroaryl is optionally substituted with one or more —R$^{12}$; and R$^{12}$ is halogen.

In some embodiments, R$^6$ is aryl optionally substituted with one or more R$^{10}$. In some embodiments, R$^6$ is phenyl optionally substituted with one or more R$^{10}$.

In some embodiments R$^5$ is —C$_1$-C$_3$ alkyl. In some embodiments, R$^5$ is methyl.

In some embodiments, R$^{10}$ is independently, at each occurrence, halogen or —OC$_1$-C$_6$ alkyl, wherein —OC$_1$-C$_6$ alkyl is optionally substituted with halogen.

In some embodiments, R$_1$ is —OR$^5$.

In some embodiments, R$^1$ is —OR$^5$, —N(R$^5$)$_2$, —NHR$^5$, or —C$_1$-C$_6$ alkyl. In some embodiments, R$^1$ is —OR$^5$. In some embodiments, R$^1$ is —OR$^5$ or —C$_1$-C$_6$ alkyl. In some embodiments, R$^5$ of R$^1$ is —C$_1$-C$_6$ alkyl. In some embodiments, R$^1$ is —OR$^5$; and R$^5$ is —C$_1$-C$_6$ alkyl. In some embodiments R$^1$ is —OCH$_3$. In some embodiments, R$^1$ is —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, or aryl. In some embodiments, R$^1$ is —C$_1$-C$_6$ alkyl. In some embodiments, R$^1$ is methyl, ethyl or propyl. In some embodiments, R$^1$ is methyl. In some embodiments, R$^1$ is —C$_2$-C$_6$ alkenyl. In some embodiments, R$^1$ is aryl.

In some embodiments, $R^5$ is —$C_1$-$C_6$ alkyl, —$C_3$-$C_8$ cycloalkyl, heterocyclyl, aryl, or heteroaryl. In some embodiments, $R^5$ is —$C_1$-$C_6$ alkyl. In some embodiments, $R^5$ is —$C_1$-$C_3$ alkyl. In some embodiments, $R^5$ is methyl. In some embodiments, $R^5$ is ethyl.

In some embodiments, $R^6$ is —$C_1$-$C_6$ alkyl, —$C_3$-$C_8$ cycloalkyl, —$C_4$-$C_8$ cycloalkenyl, heterocyclyl, or aryl. In some embodiments, $R^6$ is —$C_1$-$C_6$ alkyl optionally substituted with one or more $R^{10}$. In some embodiments, $R^6$ is aryl optionally substituted with one or more $R^{10}$. In some embodiments, $R^6$ is heteroaryl optionally substituted with one or more $R^{10}$. In some embodiments, $R^6$ is —C(O)OH. In some embodiments, $R^6$ is halogen. In some embodiments, $R^6$ is —$C_1$-$C_6$ alkyl, —$C_3$-$C_8$ cycloalkyl, —$C_4$-$C_8$ cycloalkenyl, heterocyclyl, aryl, spirocycloalkyl, spiroheterocyclyl, heteroaryl, halogen, oxo, —$(CH_2)_n$—$OR^8$, —$C(O)R^{8'}$, —$C(O)OR^8$, or —$C(O)NR^8R^9$, wherein each alkyl, cycloalkyl, heterocyclyl, spirocycloalkyl, spiroheterocyclyl, heteroaryl, or aryl is optionally substituted with one or more $R^{10}$.

In some embodiments, $R^8$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^8$ is —H. In some embodiments, $R^8$ is —$C_1$-$C_6$ alkyl, —$C_3$-$C_8$ cycloalkyl, —$C_4$-$C_8$ cycloalkenyl, heterocyclyl, or aryl, wherein $R^8$ is optionally substituted with $R^{10}$ or $R^{11}$. In some embodiments, $R^8$ is —$C_1$-$C_6$ alkyl optionally substituted with one or more $R^{10}$ or $R^{11}$. In some embodiments, $R^8$ is aryl optionally substituted with one or more $R^{10}$ or $R^{11}$. In some embodiments, $R^8$ is heteroaryl optionally substituted with one or more $R^{10}$ or $R^{11}$.

In some embodiments, $R^{8'}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^{8'}$ is —$C_1$-$C_6$ alkyl, —$C_3$-$C_8$ cycloalkyl, —$C_4$-$C_8$ cycloalkenyl, heterocyclyl, or aryl, wherein $R^{8'}$ is optionally substituted with $R^{10}$ or $R^{11}$. In some embodiments, $R^{8'}$ is —$C_1$-$C_6$ alkyl optionally substituted with one or more $R^{10}$ or $R^{11}$. In some embodiments, $R^{8'}$ is aryl optionally substituted with one or more $R^{10}$ or $R^{11}$. In some embodiments, $R^{8'}$ is heteroaryl optionally substituted with one or more $R^{10}$ or $R^{11}$.

In some embodiments, $R^9$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^9$ is —H. In some embodiments, $R^9$ is —$C_1$-$C_6$ alkyl, —$C_3$-$C_8$ cycloalkyl, —$C_4$-$C_8$ cycloalkenyl, heterocyclyl, or aryl, wherein $R^9$ is optionally substituted with $R^{10}$ or $R^{11}$. In some embodiments, $R^9$ is —$C_1$-$C_6$ alkyl optionally substituted with one or more $R^{10}$ or $R^{11}$. In some embodiments, $R^9$ is aryl optionally substituted with one or more $R^{10}$ or $R^{11}$. In some embodiments, $R^9$ is heteroaryl optionally substituted with one or more $R^{10}$ or $R^{11}$.

In some embodiments, $R^{10}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl)$_2$, —$S(O)_2NH(C_1$-$C_6$ alkyl), —$S(O)_2$ $N(C_1$-$C_6$ alkyl)$_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl)$_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$. In some embodiments, $R^{10}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, wherein $R^{10}$ is substituted with $R^{12}$. In some embodiments, $R^{10}$ is halogen. In some embodiments, $R^{10}$ is each independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$OC_3$-$C_6$ cycloalkyl, Oaryl, Oheteroaryl, —$NHC_1$-$C_6$ alkyl, —$N(C_1$-$C_6$ alkyl)$_2$, —$S(O)_2NH(C_1$-$C_6$ alkyl), —$S(O)_2N(C_1$-$C_6$ alkyl)$_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl)$_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$; wherein any two $R^{10}$ when on non-adjacent atoms, can combine to form a bridging cycloalkyl or heterocyclyl; wherein any two $R^{10}$ when on adjacent atoms, can combine to form a cycloalkyl, heterocyclyl, aryl or heteroaryl. In some embodiments, $R^{10}$ is each independently, at each occurrence halogen or —$OC_1$-$C_6$ alkyl, —$OC_3$-$C_6$ cycloalkyl, —Oaryl, -Oheteroaryl, wherein each alkyl, cycloalkyl, aryl or heteroaryl is optionally substituted with one or more —$R^{12}$.

In some embodiments, $R^{11}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl)$_2$, —$S(O)_2NH(C_1$-$C_6$ alkyl), —$S(O)_2$ $N(C_1$-$C_6$ alkyl)$_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl)$_2$, or —$N(C_1$-$C_6$ alkyl)$S(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$. In some embodiments, $R^{11}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, wherein $R^{11}$ is substituted with $R^{12}$. In some embodiments, $R^{11}$ is halogen.

In some embodiments, $R^{12}$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl)$_2$, —$S(O)_2NH(C_1$-$C_6$ alkyl), —$S(O)_2$ $N(C_1$-$C_6$ alkyl)$_2$, —$S(O)_2C_1$-$C_6$ alkyl, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$C(O)OC_1$-$C_6$ alkyl, —$N(C_1$-$C_6$ alkyl)$SO_2C_1$-$C_6$ alkyl, —$S(O)(C_1$-$C_6$ alkyl), —$S(O)N(C_1$-$C_6$ alkyl)$_2$, or —$N(C_1$-$C_6$ alkyl)$S(O)(C_1$-$C_6$ alkyl). In some embodiments, $R^{12}$ is —H. In some embodiments, $R^{12}$ is halogen.

In some embodiments, n is 1. In some embodiments, n is 2. In some embodiments, n is 3. In some embodiments, n is 4.

In some embodiments, $R^1$ is —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocycloalkyl, heteroaryl, or aryl.

Preferably, the compound is a CBP Inhibitor Compound of Formula (I) wherein $R_1$ is —$OCH_3$. In some embodiments, a CBP Inhibitor Compound of Formula (I) includes $R_1$ is —OCH$_3$ and $R_6$ is $C_6$ aryl (phenyl) optionally substituted with one or more $R_{10}$. In some embodiments, a CBP Inhibitor Compound of Formula (I) includes $R_1$ is —OCH$_3$ and $R_6$ is $C_6$ aryl (phenyl) optionally substituted with one or more $R_{10}$ being selected from the group consisting of halogen (e.g., fluorine) and methoxy, wherein the methoxy is optionally substituted with one or more $R_{12}$. In some embodiments, a CBP Inhibitor Compound of Formula (I) includes $R_1$ is —OCH$_3$ and $R_6$ is $C_6$ aryl (phenyl) optionally substituted with one or more $R_{10}$ being selected from the group consisting of halogen (e.g., fluorine) and methoxy, wherein the methoxy is optionally substituted with one or more $R_{12}$ and $R_{12}$ is a halogen (preferably, fluorine).

In some embodiments, a compound of the disclosure is a compound selected from FIG. 1, or a pharmaceutically acceptable salt thereof.

Method of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), or a pharmaceutically acceptable salt, enantiomer, hydrate, solvate, prodrug, isomer, or tautomer thereof, may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The disclosure also includes pharmaceutical compositions comprising one or more CBP Inhibitor Compounds as described herein, or a pharmaceutically acceptable salt thereof, and a pharmaceutically acceptable excipient. In some embodiments, pharmaceutical compositions reported herein can be provided in a unit dosage form (e.g., capsule, tablet or the like). Pharmaceutical compositions comprising a compound of Formula (I) can be provided in an oral dosage form such as a capsule or tablet. The oral dosage form optionally comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation. For example, a CBP Inhibitor compound of the present disclosure can be dosed at 1 mg to 1 g at a therapeutically effective frequency. The pharmaceutical compositions may be orally administered in any orally acceptable dosage form. Accordingly, a patient and/or subject can be selected for treatment using a compound described herein by first evaluating the patient and/or subject to determine whether the subject is in need of inhibition of CBP, and if the subject is determined to be in need of inhibition of CBP, then administering to the subject a composition described herein.

A pharmaceutical composition can comprise one or more compounds of Formula (I) including any compound disclosed in the examples below, as provided herein. In one example, an active pharmaceutical ingredient (API) can comprise about 90% or more of a compound of Formula (I) and up to about 10% (preferably up to about 5%, most preferably up to about 2.5% including about 1.5%) of the compound of Formula (I). Oral dosage forms comprising a compound of Formula (I) can be prepared as a drug-in-capsule (DiC), encapsulated simple dry-blend granulation, and lipid-based solution in hard shell capsule. The capsules can contain pharmaceutically acceptable excipients, and encapsulated capsules can be packaged in high-density polyethylene induction sealed bottles.

EXAMPLES

Definitions Used in the Following Schemes and Elsewhere Herein are:
    ACN acetonitrile
    Ac$_2$O acetic anhydride
    (±)BINAP (±)-2,2'-Bis(diphenylphosphino)-1,1'-binaphthalen
    Boc tert-butoxycarbonyl
    n-BuOH butanol
    cm centimeter
    DCE 1,2-dichloroethane
    DCM dichloromethane or methylene chloride
    DEA diethylamine
    DMC 2-Chloro-4,5-dihydro-1,3-dimethyl-1H-imidazolium chloride
    DMP Dess-Martin periodinane
    DMTMM 4-(4,6-Dimethoxy-1,3,5-triazin-2-yl)-4-methylmorpholinium chloride
    DIEA N,N-diisopropylethylamine
    DMAP 4-(dimethylamino)pyridine
    DMF N,N-dimethylformamide
    DMSO dimethylsulfoxide
    DPPA diphenylphosphoryl azide
    dppf bis(diphenylphosphino)ferrocene
    ES electrospray ionization
    Et$_3$N triethylamine
    EtOAc ethyl acetate
    EtOH ethanol
    FA formic acid
    FCC flash column chromatography
    h hours
    HATU 2-(3H-[1,2,3]triazolo[4,5-b]pyridin-3-yl)-1,1,3,3-tetramethylisouronium hexafluorophosphate
    HCl hydrogen chloride
    HOAc acetic acid
    HPLC high performance liquid chromatography
    (i-Pr)$_2$NEt N,N-diisopropylethylamine
    L liter LC/MS liquid chromatography/mass spectrometry
LDA lithium diisopropylamine
$K_2CO_3$ potassium carbonate
MeOH methanol
mL milliliter
mmol millimole
mg milligram
MHz megahertz
MS mass spectrometry
m/z mass/charge ratio
NBS N-bromosuccinimide
nm nanometer
NMM 4-methylmorpholine
NMR nuclear magnetic resonance
$Pd_2(dba)_3$ tris(dibenzylideneacetone)dipalladium
$Ph_3P$ triphenylphosphine
PhCHO benzaldehyde
PhMe toluene
ppm parts per million
rt room temperature
RT retention time
SFC supercritical fluid chromatography
STAB sodium triacetoxyborohydride
p-TSA para-toluenesulfonic anhydride
p-TsOH para-toluenesulfonic acid
TFA trifluoroacetic acid
TFAA trifluoroacetic anhydride
THF tetrahydrofuran
UV ultraviolet
XPhos 2-dicyclohexylphosphino-2',4',6'-triisopropylbiphenyl Materials Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 μm 2.1×50 mm; gradient: 5-100% Solvent B (95/5/0.09%:Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 μm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

General Methods of Compound Preparation

Described herein are methods of synthesizing the compounds of the present disclosure. Compounds of the present disclosure can be synthesized according to the synthetic schemes provided below. Preparation of the starting material for Schemes 1 and 2 ("Intermediate 1") is described below. Preparation of the starting material for Schemes 3 and 4 can be found in Example 1, Part A of U.S. Pat. No. 4,404,207.

Unless otherwise specified, the substituents $R^2$ and $R^3$ in the following reaction schemes are defined as follows, and $R^6$ is as defined in the description and claims.

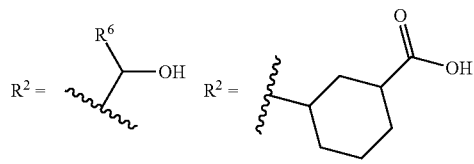

Scheme 1 provides methods useful for synthesizing compounds of Formula I.

Scheme 1

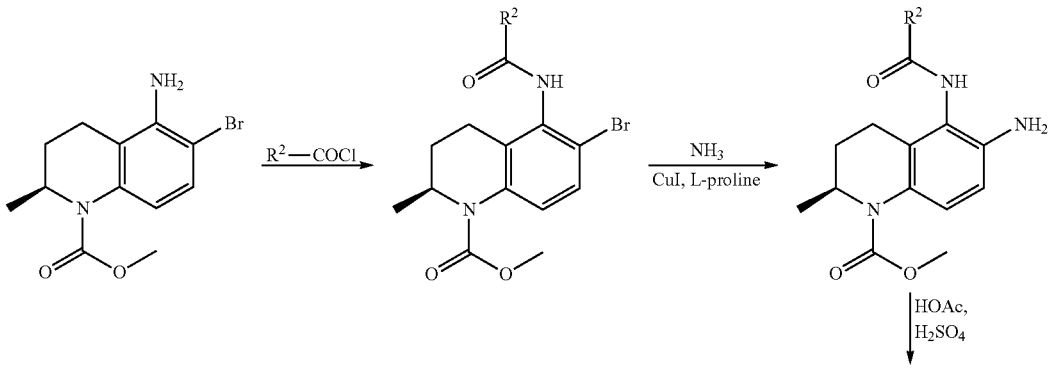

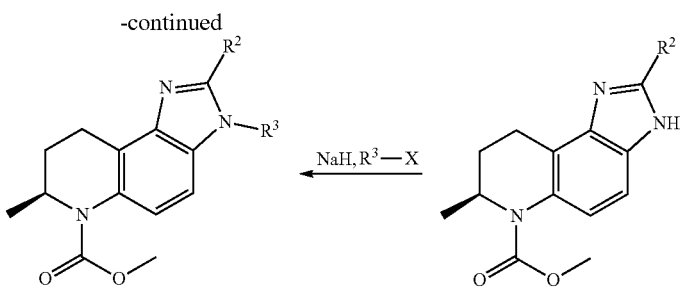
Scheme 2 provides methods useful for synthesizing compounds of Formula I.
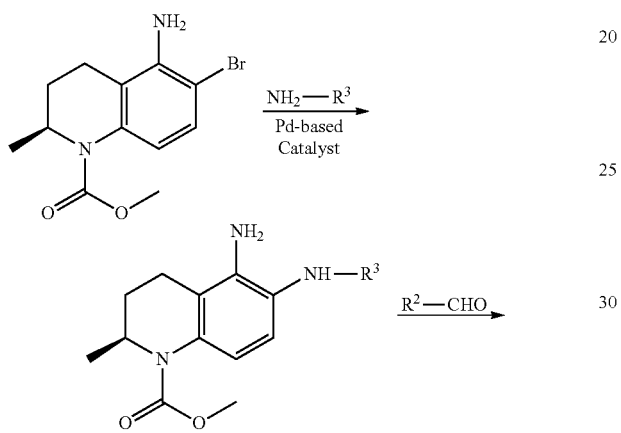
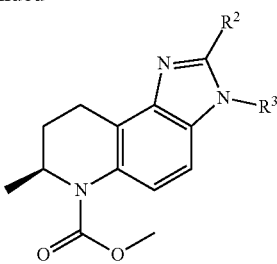
Alternatively, Scheme 3 provides methods useful for synthesizing certain compounds of Formula I.
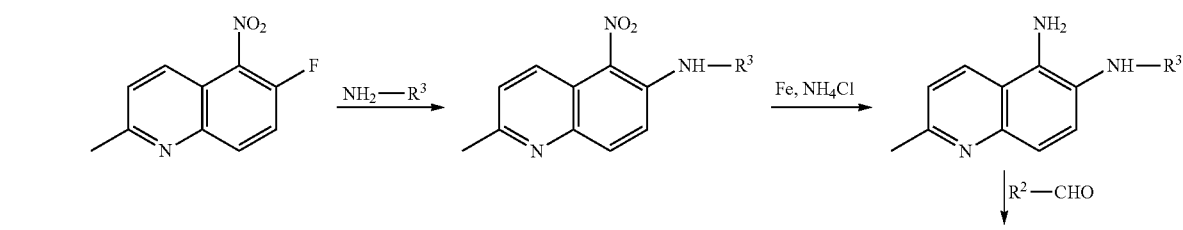
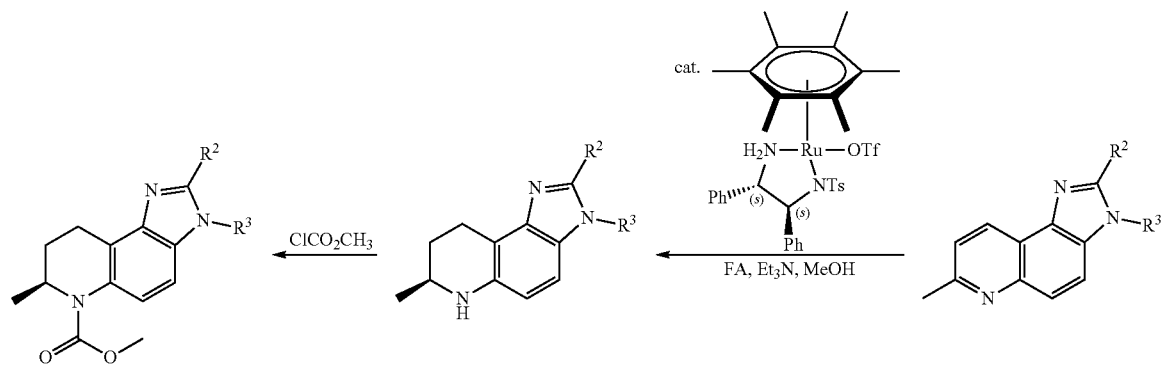

Alternatively, Scheme 4 provides methods useful for synthesizing certain compounds of Formula I.
Scheme 4
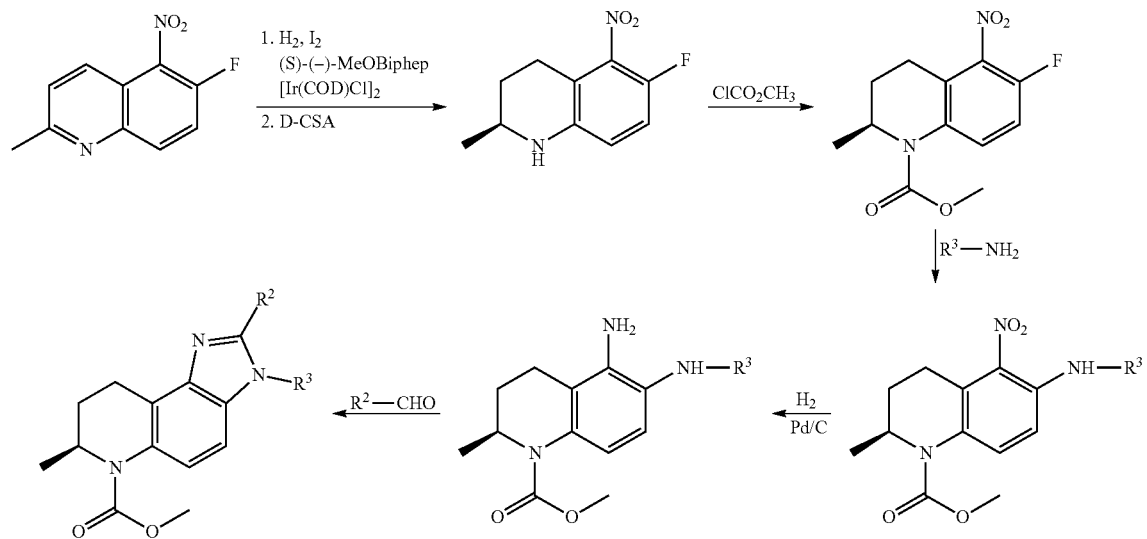
Preparation of Intermediate 1: methyl (S)-5-amino-6-bromo-2-methyl-3,4-dihydroquinoline-1(2H)-carboxylate
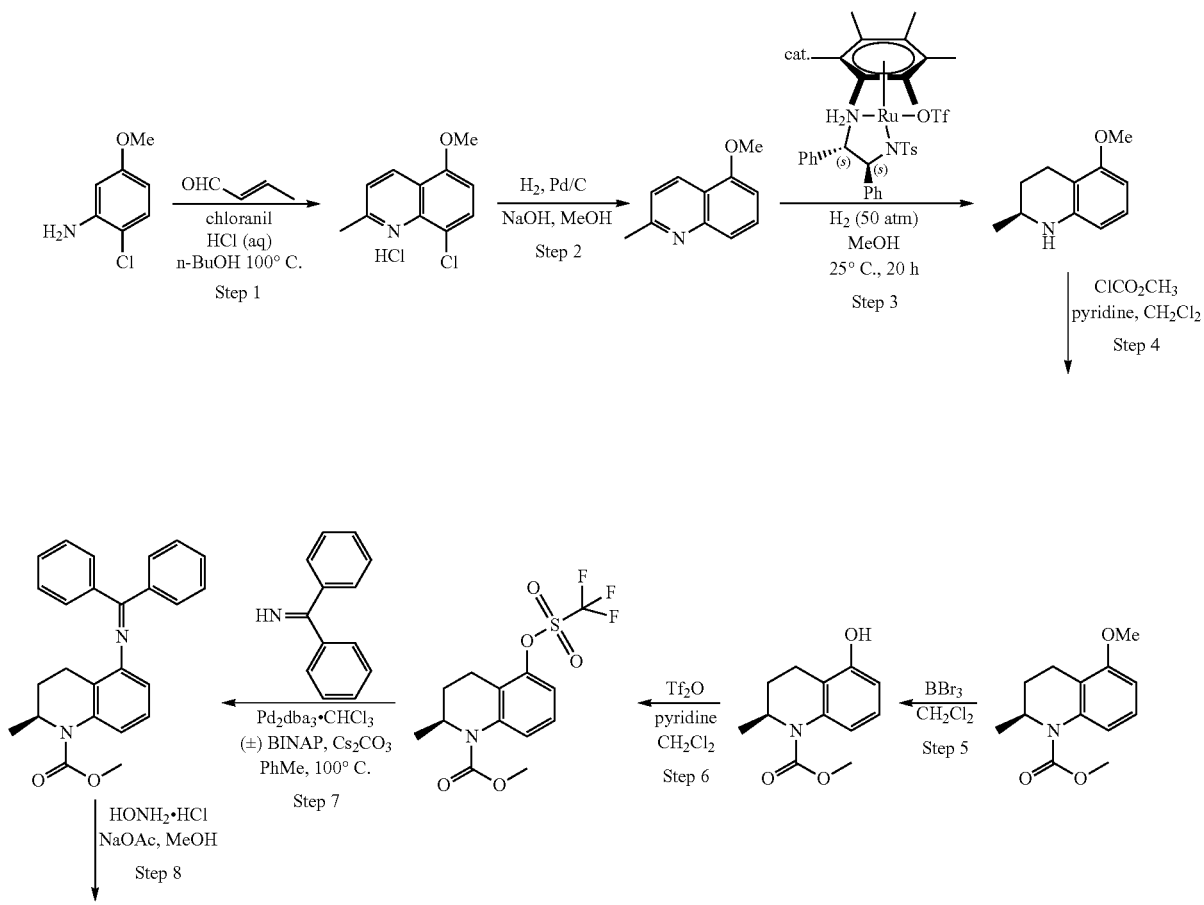

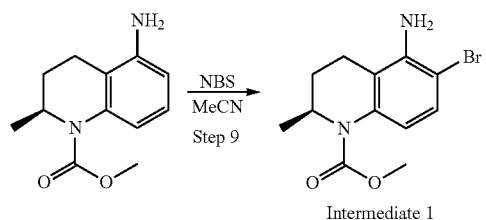

Intermediate 1

Step 1. 8-chloro-5-methoxy-2-methylquinoline Hydrochloride

Into a 5 L 4-necked round-bottom flask purged and maintained with an inert atmosphere of nitrogen, 2-chloro-5-methoxyaniline (250 g, 1.59 mol) was dissolved in 1-butanol (1200 mL). Then hydrochloric acid (aq, 36.5%, 526.5 mL) and chloranil (456.5 g, 1.86 mol) were added. The resulting mixture was stirred for 1 h at 100° C. under nitrogen atmosphere. Then a solution of (E)-but-2-enal (169 mL, 2.06 mol) in 1-butanol (300 mL) was added dropwise. The resulting solution was stirred for 1 h at 100° C. under nitrogen atmosphere. The oil bath was cooled to 70° C. and tetrahydrofuran (1500 mL) was added. Then the resulting mixture was stirred for 1 h at 70° C. The reaction mixture was cooled to 0° C. and the solids were filtered. The solids were washed with tetrahydrofuran (3 L) at 0° C. This afforded the title compound (300 g, 77%) as a yellow solid. MS: (ES, m/z): 208, 210 [M+H]+. then dried in an oven to afford 8-chloro-5-methoxy-2-methylquinoline hydrochloride (83.0 g, 74%) as a yellow solid. MS (ES, m/z): 208 [M+H]+.

Step 2. 5-methoxy-2-methylquinoline

Into a 1000-mL 3-necked round-bottom flask, 8-chloro-5-methoxy-2-methylquinoline hydrochloride (50 g, 204.82 mmol) was dissolved in methanol (300 mL). Then sodium hydroxide (3 M, 205 mL) and 10% palladium on carbon (25 g) were added. Hydrogen (g) was charged into the reaction mixture. The reaction mixture was stirred under a hydrogen atmosphere for 3 h at room temperature. The reaction was vented to nitrogen and the solids were filtered out over celite. The filtered solution was concentrated under vacuum. The residue was subjected to purification by FCC eluting with ethyl acetate/petroleum ether (1:5). This afforded the title compound (28.5 g, 80%) as a yellow oil. MS: (ES, m/z): 174 [M+H]+.

Step 3. (2S)-5-methoxy-2-methyl-1,2,3,4-tetrahydroquinoline

Into a 30-mL pressure tank reactor (50 atm), 5-methoxy-2-methylquinoline (4.0 g, 23.09 mmol) was dissolved in methanol (10 mL). Then Ru(OTf)(η6-hexamethylbenzene)((S,S)-TsDPEN) ([N-[(1S,2S)-2-(amino-κN)-1,2-diphenylethyl]-4-methylbenzenesulfonamidato-κN][(1,2,3,4,5,6-η)-1,2,3,4,5,6-hexamethylbenzene](1,1,1-trifluoromethanesulfonato-κO)-ruthenium, prepared according to the procedure in *J. Am. Chem. Soc.* 2011, 133, 9878-9891) (150 mg, 0.23 mmol) was added. To the above hydrogen was introduced in. The resulting solution was stirred for 6 h at room temperature. The resulting mixture was concentrated under vacuum. The residue was subjected to purification by FCC eluting with ethyl acetate/petroleum ether (1:4). This afforded the title compound (3.0 g, 73%) as a yellow oil. MS: (ES, m/z): 178 [M+H]+.

Step 4. methyl (S)-5-methoxy-2-methyl-3,4-dihydroquinoline-1(2H)-carboxylate Into a 250-mL round-bottom flask, (2S)-5-methoxy-2-methyl-1,2,3,4-tetrahydroquinoline (18 g, 99.52 mmol) was dissolved in dichloromethane (100 mL). Then pyridine (23.6 g, 298.36 mmol) was added, followed by methyl carbonochloridate (9.4 g, 99.47 mmol). The resulting solution was stirred for 1 h at room temperature. The resulting solution was diluted with 100 mL of dichloromethane and washed with 3×200 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (21 g, 89%) as a yellow oil. MS: (ES, m/z): 236 [M+H]+.

Step 5. methyl (S)-5-hydroxy-2-methyl-3,4-dihydroquinoline-1(2H)-carboxylate Into a 500-mL 3-necked round-bottom flask, methyl (2S)-5-methoxy-2-methyl-1,2,3,4-tetrahydroquinoline-1-carboxylate (21 g, 89.36 mmol) was dissolved in dichloromethane (150 mL). Then boron tribromide (150 mL, 0.15 mol, 1 M in CH$_2$Cl$_2$) was added. The resulting solution was stirred for 1 h at room temperature. The reaction was then quenched by the addition of 300 mL of water. The resulting mixture was extracted with 3×300 mL of dichloromethane. The organic layers were combined, dried over anhydrous sodium sulfate, filtered and concentrated under vacuum. The residue was subjected to purification by FCC eluting with ethyl acetate/petroleum ether (1:2). This afforded the title compound (13.5 g, 68%) as a yellow solid. MS: (ES, m/z): 222 [M+H]+.

Step 6. methyl (S)-2-methyl-5-(((trifluoromethyl)sulfonyl)oxy)-3,4-dihydroquinoline-1(2H)-carboxylate Into a 250-mL round-bottom flask, methyl (2S)-5-hydroxy-2-methyl-1,2,3,4-tetrahydroquinoline-1-carboxylate (5 g, 18.08 mmol) was dissolved in dichloromethane (50 mL). Then pyridine (14.3 g, 180.78 mmol) and trifluoromethanesulfonic anhydride (10.2 g, 36.15 mmol) were added. The resulting solution was stirred for 1 h at room temperature. The resulting mixture was washed with 3×100 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (5.5 g, 86%) as a yellow oil. MS: (ES, m/z): 354 [M+H]+.

Step 7. methyl (S)-5-((diphenylmethylene)amino)-2-methyl-3,4-dihydroquinoline-1(2H)-carboxylate Into a 500-mL round-bottom flask purged and maintained with an inert atmosphere of nitrogen, methyl (2S)-2-methyl-5-[(trifluoromethane)sulfonyloxy]-1,2,3,4-tetrahydroquinoline-1-carboxylate (23.5 g, 65.18 mmol) was dissolved in toluene (100 mL). Then diphenylmethanimine (17.9 g, 97.78 mmol), tris(dibenzylideneacetone)dipalladium-chloroform adduct (1.19 g, 1.30 mmol), (+/−)-2,2'-Bis(diphenylphosphino)-1,1'-binaphthyl (2.43 g, 3.90 mmol) and cesium carbonate (42.4 g, 130.13 mmol) were added. The resulting solution was stirred overnight at 100° C. under nitrogen atmosphere. The reaction mixture was cooled and the solids were filtered out. The residue was subjected to purification by FCC eluting with ethyl acetate/petroleum ether (1:3). This afforded the title compound (33 g, 80%) as a yellow oil. MS: (ES, m/z): 385 [M+H]$^+$.

Step 8. methyl (S)-5-amino-2-methyl-3,4-dihydroquinoline-1(2H)-carboxylate

Into a 500-mL round-bottom flask, methyl (2S)-5-[(diphenylmethylidene)amino]-2-methyl-1,2,3,4-tetrahydroquinoline-1-carboxylate (33 g, 85.93 mmol) was dissolved in methanol (200 mL). Then sodium acetate (17 g, 207.23 mmol) and hydroxylamine hydrochloride (12.3 g, 177.00 mmol) were added. The resulting solution was stirred for 2 h at room temperature. The solids were filtered out. The resulting mixture was concentrated under vacuum. The residue was subjected to purification by FCC eluting with ethyl acetate/petroleum ether (1:2). This afforded the title compound (12.5 g, 66%) as a yellow solid. MS: (ES, m/z): 221 [M+H]$^+$.

Step 9. methyl (S)-5-amino-6-bromo-2-methyl-3,4-dihydroquinoline-1(2H)-carboxylate (Intermediate 1)

Into a 100-mL 3-necked round-bottom flask, methyl (2S)-5-amino-2-methyl-1,2,3,4-tetrahydroquinoline-1-carboxylate (1 g, 4.09 mmol) was dissolved in acetonitrile (20 mL). Then N-bromosuccinimide (730 mg, 4.10 mmol) was added. The resulting solution was stirred for 30 min at room temperature. The resulting mixture was concentrated under vacuum. The residue was subjected to purification by FCC eluting with ethyl acetate/petroleum ether (1:1). This afforded the title compound (1.1 g, 90%) as a yellow solid. MS: (ES, m/z): 299, 301 [M+H]$^+$.

H-NMR: (400 MHz, CD3OD, ppm): 7.19 (d, J=8.8 Hz, 1H), 6.84 (d, J=8.8 Hz, 1H), 4.73-4.69 (m, 1H), 3.74 (s, 3H), 2.64-2.57 (m, 1H), 2.55-2.44 (m, 1H), 2.12-2.05 (m, 1H), 1.82-1.79 (m, 1H), 1.17 (d, J=6.9 Hz, 3H).

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The synthetic schemes are presented for the synthesis of certain compounds herein disclosed. The process and results for the assays testing BET family bromodomain inhibition are also described.

Example 1: methyl (S)-2-(2-(1H-pyrazol-1-yl)ethyl)-7-methyl-3-(2-(((1-methyl-1H-pyrazol-3-yl)methyl)amino)ethyl)-3,7,8,9-tetrahydro-6H-imidazo[4,5-f]quinoline-6-carboxylate

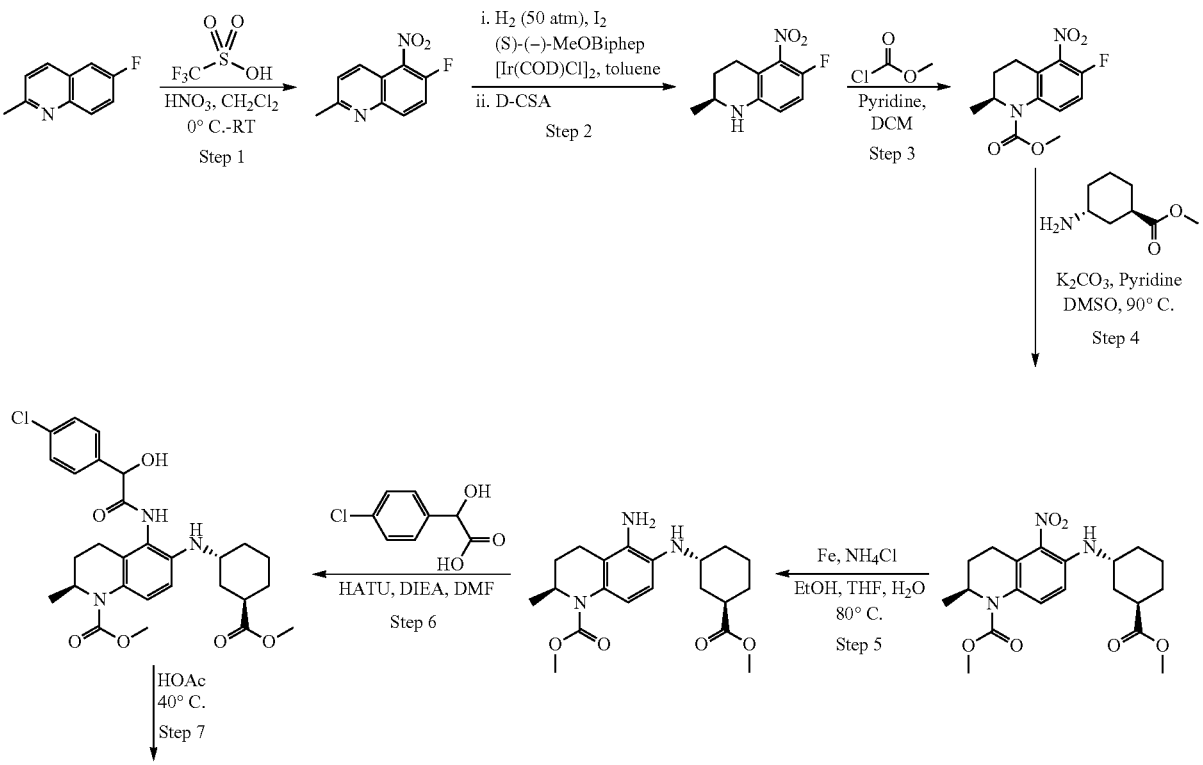

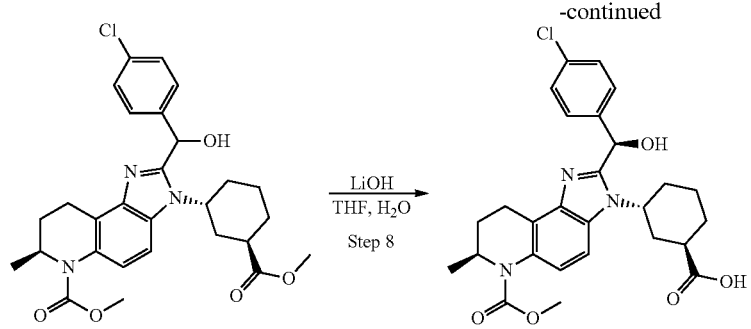 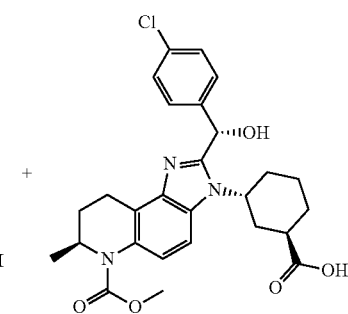

Step 1. 6-fluoro-2-methyl-5-nitroquinoline

A solution of trifluoromethanesulfonic acid (82.0 mL, 0.923 mol) in HNO₃ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 hours at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]⁺.

Step 2. (2S)-6-fluoro-2-methyl-5-nitro-1,2,3,4-tetrahydroquinoline

A solution of (S)-(−)-MeO-BIPHEP (1.03 mg, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of I₂ (410 mg, 1.62 mmol), and 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers was dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]⁺.

Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), and methyl carbonochloridate (18.7 mL, 0.242 mol) in dichloromethane (150 mL) was stirred for 3 h at room temperature (25° C.). The reaction was washed with 1N hydrogen chloride (aq., 2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]⁺.

Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), and methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 [M+H]⁺.

Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-2-methyl-5-nitro-6-[[(1R,3R)-4-(methoxycarbonyl)cyclohexyl]amino]-1,2,3,4-tetrahydroquinoline-1-carboxylate (31.0 g, 76.46 mmol), NH₄Cl (24.3 g, 454.28 mmol), and Fe (powder, 64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]⁺.

Step 6. methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate A solution of 2-(4-chlorophenyl)-2-hydroxyacetic acid (112 mg, 0.60 mmol), HATU (304 mg, 0.80 mmol), methyl (2S)-5-amino-6-[[(1R,3R)-3-(methoxycarbonyl)cyclohexyl]amino]-2-methyl-1,2,3,4-tetrahydroquinoline-1-carboxylate (150 mg, 0.40 mmol), and DIEA (155 mg, 1.20 mmol) in N,N-dimethylformamide (2 mL) was stirred for 15 h at room temperature (25° C.). The resulting solution was diluted with water (30 mL), and extracted with ethyl acetate (3×50 mL). The organic layers were combined and washed with brine (2×25 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate as yellow oil (70.0 mg, 32%). LCMS (ES, m/z): 544 [M+H]$^+$.

Step 7. methyl (7S)-2-[(4-chlorophenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate (60.0 mg, 0.11 mmol) in AcOH (2 mL) was stirred for 15 h at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(4-chlorophenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate as yellow oil (46.0 mg, 79%). LCMS (ES, m/z): 526 [M+H]$^+$.

Step 8. (1R,3R)-3-[(7S)-2-[(R)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid (PH-FMA-PJ00136-1145-0A); (1R,3R)-3-[(7S)-2-[(S)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[(4-chlorophenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate (50.0 mg, 0.10 mmol), and LiOH (11.4 mg, 0.48 mmol) in tetrahydrofuran (1 mL) and water (1 mL) was stirred for 15 h at 25° C. The resulting mixture was concentrated under vacuum. The crude product was purified by Prep-HPLC (Column: XBridge Shield RP18 OBD Column, Sum, 19×150 mm; Mobile Phase, A: water (containing 10 mmol/L NH$_4$HCO$_3$) and B: ACN (10% to 37% over 12 min); Detector: UV 254 nm). The product fractions were lyophilized to afford (1R,3R)-3-[(7S)-2-[(R)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid (413) as a white solid (10.5 mg, 43%); and (1R,3R)-3-[(7S)-2-[(S)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid (501) as a white solid (7.0 mg, 29%).

First eluting isomer (413): $^1$H-NMR (CD$_3$OD, 400 MHz) δ (ppm): 7.49 (d, J=9.0 Hz, 1H), 7.42-7.33 (m, 5H), 6.19 (s, 1H), 4.92-4.90 (m, 1H), 4.82-4.72 (m, 1H), 3.79 (s, 3H), 3.34-3.20 (m, 1H), 3.02-2.94 (m, 1H), 2.90-2.87 (m, 1H), 2.36-2.09 (m, 4H), 1.99-1.96 (m, 1H), 1.80-1.42 (m, 5H), 1.16 (d, J=6.6 Hz, 3H). LCMS (ES, m/z): 512 [M+H]$^+$.

Second eluting isomer (501): $^1$H-NMR (CD$_3$OD, 400 MHz) δ (ppm): 7.52-7.33 (m, 6H), 6.22 (s, 1H), 4.84-4.73 (m, 2H), 3.78 (s, 3H), 3.27-3.16 (m, 1H), 3.04-2.92 (m, 1H), 2.90-2.88 (m, 1H), 2.46-2.35 (m, 2H), 2.30-2.22 (m, 1H), 2.15-2.02 (m, 2H), 1.82-1.71 (m, 1H), 1.63-1.55 (m, 2H), 1.40-1.28 (m, 1H), 1.15 (d, J=6.6 Hz, 4H). LCMS (ES, m/z): 512 [M+H]$^+$.

The compounds listed in FIG. 1 were prepared using standard chemical manipulations and procedures similar to those described herein. In FIG. 1, "Eluted Isomer" refers to the order in which the compound eluted by preparative HPLC.

Example 2: Compounds 424 and 660: (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (424); (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (660)

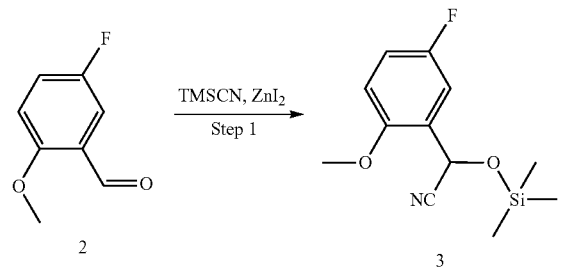

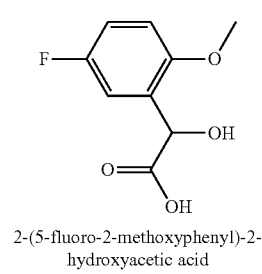

2-(5-fluoro-2-methoxyphenyl)-2-hydroxyacetic acid

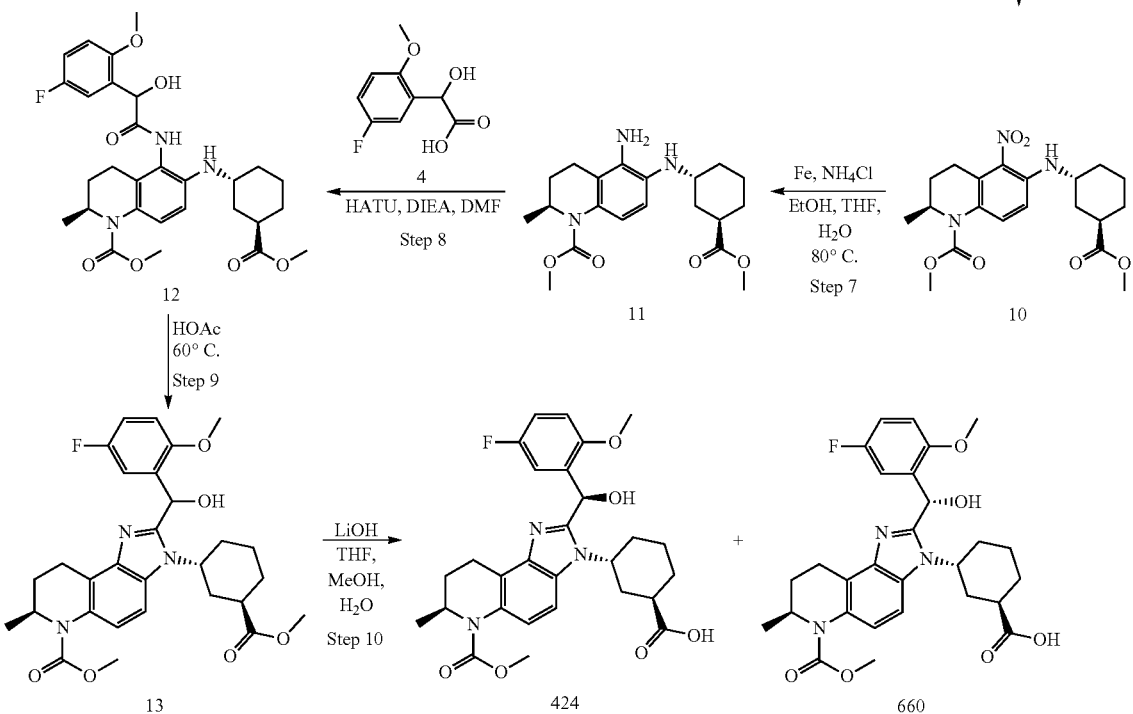

Step 1. 2-(5-fluoro-2-methoxyphenyl)-2-[(trimethylsilyl)oxy]acetonitrile

A solution of $ZnI_2$ (1.6 mg, 0.01 mmol), 5-fluoro-2-methoxybenzaldehyde (1.54 g, 9.99 mmol) in trimethylsilanecarbonitrile (1.5 mL, 11.25 mmol) was stirred for 1 h at room temperature. The resulting mixture was concentrated under vacuum. The resulting crude product was purified by silica gel chromatography (eluting with 1:1 ethyl acetate/petroleum ether) to afford 2-(5-fluoro-2-methoxyphenyl)-2-[(trimethylsilyl)oxy]acetonitrile as a white solid (2.0 g, 79%).

Step 2. 2-(5-fluoro-2-methoxyphenyl)-2-hydroxyacetic Acid

A solution of 2-(5-fluoro-2-methoxyphenyl)-2-[(trimethylsilyl)oxy]acetonitrile (1.50 g, 5.92 mmol) in hydrochloric acid (10 mL, 12 M) was stirred for 1 h at 25° C., and then stirred for 2 h at 70° C. The reaction mixture was cooled and concentrated under vacuum. The crude product was purified by reverse phase chromatography (Column: C18; Mobile phase, A: water (containing 0.05% TFA) and B: ACN (5% to 20% over 30 min); Detector, UV 254 nm) to afford 2-(5-fluoro-2-methoxyphenyl)-2-hydroxyacetic acid as a white solid (1.10 g, 93%).

Step 3. 6-fluoro-2-methyl-5-nitroquinoline

A solution of trifluoromethanesulfonic acid (82.0 mL, 0.923 mol) in $HNO_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]$^+$.

Step 4. (2S)-6-fluoro-2-methyl-5-nitro-1,2,3,4-tetrahydroquinoline

A solution of (S)-(–)-MeO-BIPHEP (1.03 mg, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of I$_2$ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]$^+$.

Step 5. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1 M hydrochloric acid (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]$^+$.

Step 6. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl) cyclohexyl] amino]-2-methyl-5-nitro-1,2,3,4-tetrahydroquinoline-1-carboxylate as a red oil (32 g, 72%). LCMS (ES, m/z): 406 [M+H]$^+$.

Step 7. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), and water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 8. methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate A solution of 2-(5-fluoro-2-methoxyphenyl)-2-hydroxyacetic acid (240 mg, 1.20 mmol), HATU (228 mg, 0.60 mmol), methyl (2S)-5-amino-6-[[(1R,3R)-3-(methoxycarbonyl) cyclohexyl]amino]-2-methyl-1,2,3,4-tetrahydroquinoline-1-carboxylate (150 mg, 0.40 mmol), DIEA (0.19 mL, 1.20 mmol) in N,N-dimethylformamide (10 mL) was stirred for 1 h at 25° C. The resulting solution was diluted with H$_2$O (10 mL). The resulting solution was extracted with ethyl acetate (3×15 mL) and the organic layers combined. The resulting mixture was washed with brine (2×20 mL). The mixture was dried over anhydrous sodium sulfate and concentrated under vacuum. The resulting crude product was purified by silica gel chromatography (eluting with 3:2 ethyl acetate/petroleum ether) to afford methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetra-hydroquinoline-1-carboxylate as a yellow solid (180 mg, 81%). LCMS (ES, m/z): 558 [M+H]$^+$.

Step 9. methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate (180 mg, 0.32 mmol) in AcOH (8 mL) was stirred for overnight at 60° C. The reaction mixture was cooled and concentrated under vacuum. The resulting crude product was purified by silica gel chromatography (eluting with 1:1 ethyl acetate/petroleum ether) to afford methyl (7S)-2-[(5-fluoro-2-methoxyphenyl)(hydroxy)methyl]-3-[(1R,3R)-3-(methoxycarbonyl)cyclohexyl]-7-methyl-3H, 6H,7H,8H,9H-imidazo[4,5-f]quinoline-6-carboxylate as a yellow solid (120 mg, 69%). LCMS (ES, m/z): 540 [M+H]⁺.

Step 10. (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid; (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic Acid A solution of methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate (120 mg, 0.22 mmol), and LiOH (16 mg, 0.67 mmol) in tetrahydrofuran (2.0 mL), methanol (2.0 mL) and water (2.0 mL) was stirred overnight at 25° C. The resulting mixture was concentrated under vacuum. The crude product was purified by Prep-HPLC (Column, XBridge Prep C18 OBD Column, 19×150 mm, 5um; Mobile phase, A: water (containing 10 mmol/L NH₄HCO₃) and B: ACN (15.0% to 29.0% over 14 min); Detector, UV 220/254 nm). The product was separated by Chiral-Prep-HPLC (Column, CHIRALPAK IE, 2×25 cm, 5 um; Mobile phase, A: Hex (containing 0.1% FA) and B: ethanol (hold 50.0% ethanol over 12 min); Detector, UV 220/254 nm). The product fractions were concentrated to afford (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (23.6 mg, 20%); and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (23.8 mg, 20%). Stereoisomeric purity was determined via HPLC: Column: CHIRALPAK IE-3, Column size: 0.46×5 cm; 3 µm; Mobile phase: Hex (0.1% FA): EtOH=50:50, Flow: 1.0 ml/min.

First eluting isomer (424): 1H-NMR (CD3OD, 400 MHz) δ (ppm): 7.56-7.47 (m, 1H), 7.47-7.31 (m, 1H), 7.21-7.09 (m, 1H), 7.09-6.89 (m, 2H), 6.53 (s, 1H), 4.81-4.61 (m, 2H), 3.85 (s, 3H), 3.78 (s, 3H), 3.31-3.18 (m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.16 (d, J=6.8 Hz, 3H). LCMS (ES, m/z): 526 [M+H]⁺.

Second eluting isomer (660): 1H-NMR (CD3OD, 400 MHz) δ (ppm): 7.69-7.44 (m, 2H), 7.44-7.29 (m, 1H), 7.12-6.99 (m, 1H), 6.98-6.82 (m, 1H), 6.37 (s, 1H), 5.03-4.91 (m, 1H), 4.81-4.69 (m, 1H), 3.78 (s, 3H), 3.61 (s, 3H), 3.22-3.04 (m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J=6.4 Hz, 3H). LCMS (ES, m/z): 526 [M+H]⁺.

In a preferred embodiment the disclosure provides the first eluting isomer obtained from Step 10 of the process described in Example 2 above, or a pharmaceutically acceptable salt thereof. In a preferred embodiment the disclosure provides compound 424 having the following structure:

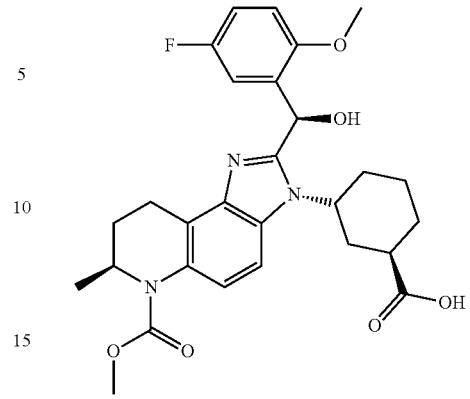

(Compound 424)

or a pharmaceutically acceptable salt, hydrate, solvate, or tautomer thereof.

In some embodiments, the disclosure provides a pharmaceutical composition comprising compound 424 of the foregoing structure or a pharmaceutically acceptable salt thereof, at a purity of at least 90%, for example greater than 90%, 91%, 92%, 93%, 94%, 95%, 96%, 97%, 98%, or 99% relative to one or more of its related stereoisomers. For example, the disclosure provides the compound 424 of the foregoing structure or a pharmaceutically acceptable salt thereof, at a purity of at least 90%, e.g. greater than 90%, 91%, 92%, 93%, 94%, 95%, 96%, 97%, 98%, or 99% purity relative to compound 660 and optionally other stereoisomers of compound 424 depicted below. In some embodiments, the disclosure provides a pharmaceutical composition comprising compound 424 of the foregoing structure or a pharmaceutically acceptable salt thereof, at a purity of at least 95%.

A composition of Formula (I) can comprise a compound of one or more of Formula (I-a), (I-b), (I-c), (I-d), (I-e), (I-f), (I-g), (I-h), (I-i), (I-j), (I-k), (I-l), (I-m), (I-n), and/or (I-o). For example, in some embodiments the disclosure provides a composition comprising compound 424 of the foregoing structure or a pharmaceutically acceptable salt thereof at a purity of at least 90% wherein the composition comprises less than 10%, e.g. less than 9%, less than 8%, less than 7%, less than 6%, less than 5%, less than 4%, less than 3%, less than 2% or less than 1%, collectively of one or more of the following stereoisomers of compound 424, represented as Formulae (II-a)-(II-o) below:

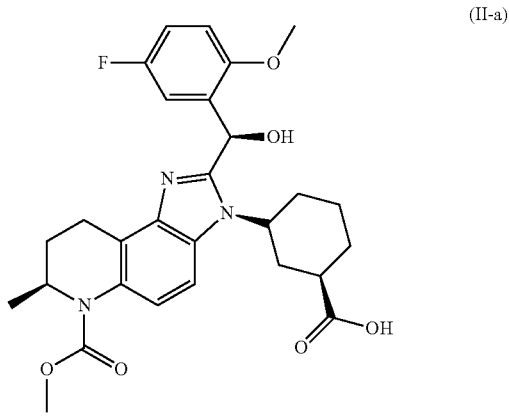

(II-a)

-continued
(II-b)
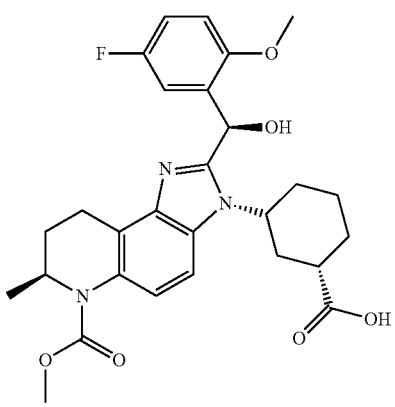
(II-c)
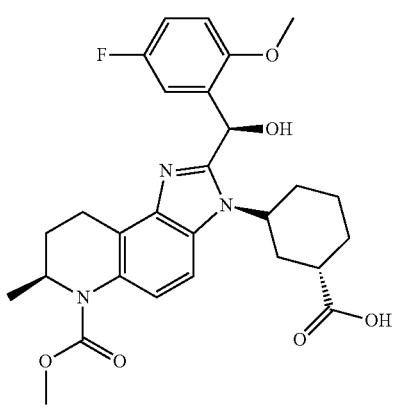
(II-d)
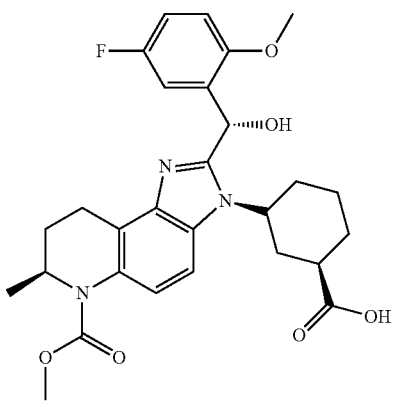
(II-e)
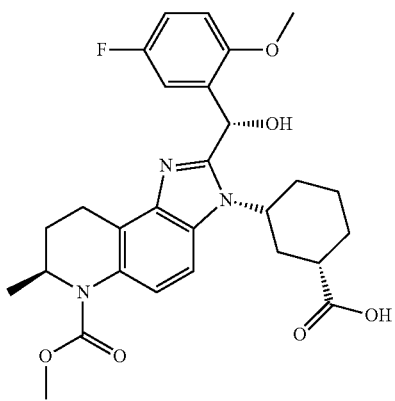
(II-f)
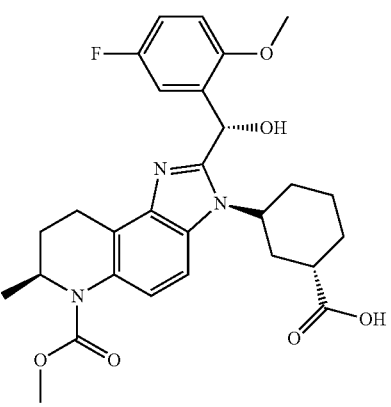
(II-g)
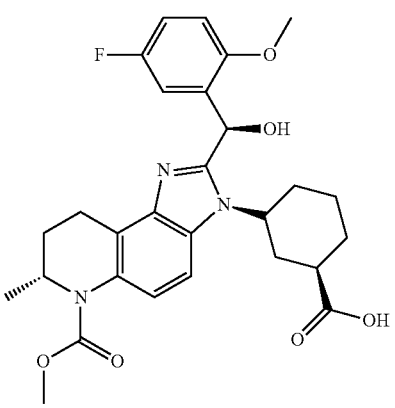
(II-h)
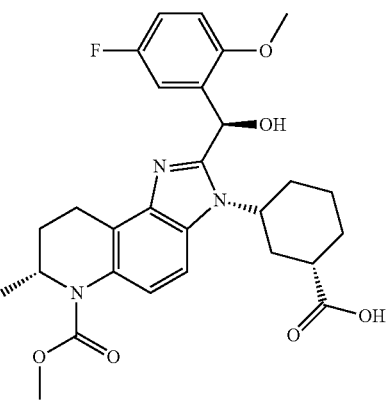
(II-i)
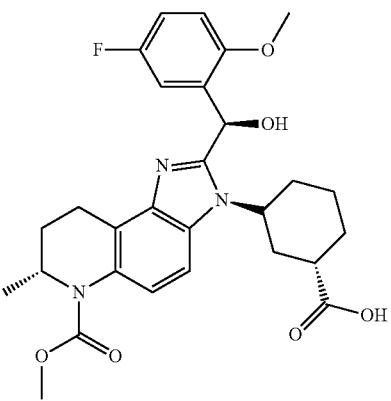

(II-j)

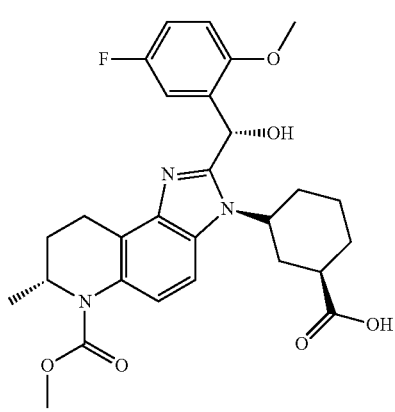

(II-k)

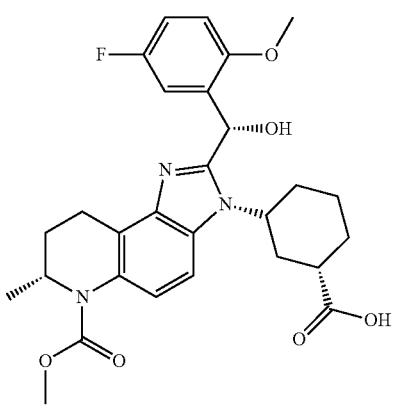

(II-l)

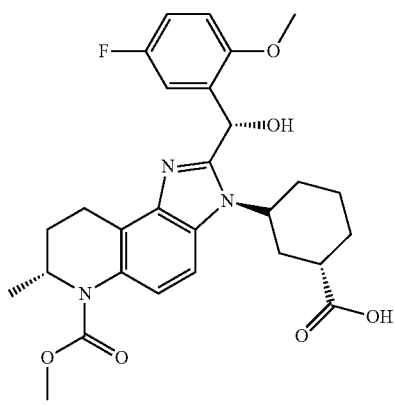

(II-m)

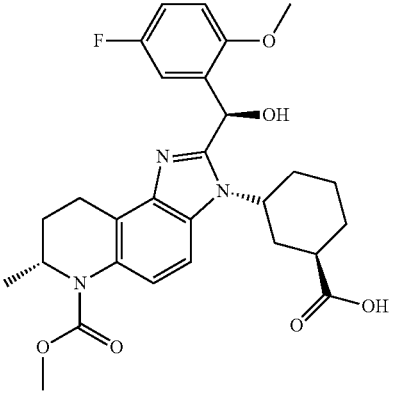

(II-n)

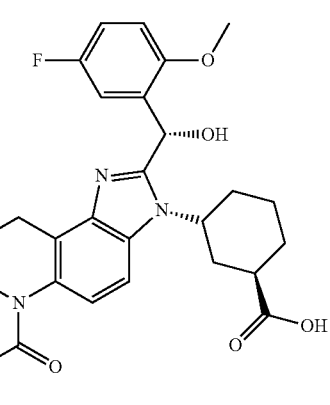

(II-o)/compound 660

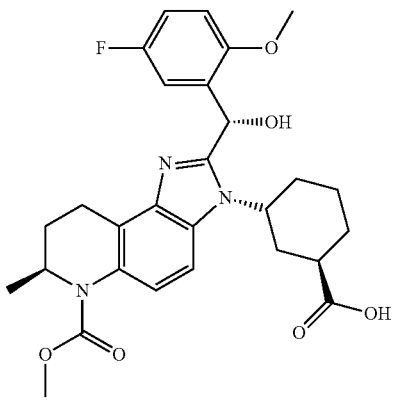

In any of the foregoing embodiments, the percentage purity recited may be determined by HPLC. In some embodiments the percentage purity is determined using the following HPLC method:

| |
| --- |
| Sample Preparation: |
| Prepare 0.2 mg/mL in 70/30 Water/Acetonitrile. LCMS Information: Instruments: |
| MS: Waters QDa MS HPLC: Waters Alliance e2695 UV: Waters 2998 PDA Conditions: |
| Mobile Phase A: 10 mM Ammonium acetate Mobile Phase B: Acetonitrile Column: Waters XSelect Phenyl-Hexyl, 3.5 μm, 4.6 × 150 mm Column Temperature: 35° C. LC Gradient: |
| LC Flow Rate: 1 mL/min UV Wavelength: 238 nm Ionization Mode: Electrospray Ionization +ive Injection Volume: 8 μL |

For instance, the disclosure provides a pharmaceutical composition comprising compound 424 or a pharmaceutically acceptable salt thereof at a purity of at least 95% as determined by the above HPLC method. The disclosure also provides a pharmaceutical composition comprising compound 424 at a purity of at least 95% as determined by the above HPLC method.

The disclosure provides a compound of Formula II obtained by the foregoing method exemplified in Example 2:

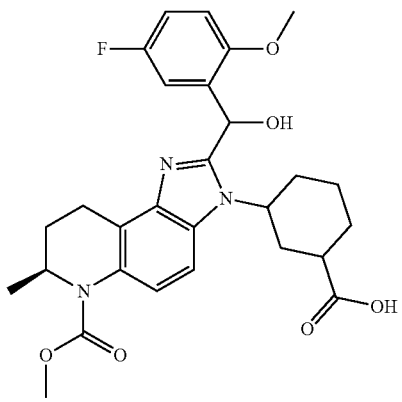

(II)

or a pharmaceutically acceptable salt, enantiomer, hydrate, solvate, isomer or tautomer thereof.

It will be apparent to the skilled reader that each of the stereoisomers of the compound of Formula (II) can be obtained by varying the stereochemistry of the appropriate reagents utilized in the method of Example 2 above. For instance, by adjusting the reagent used in Step 4 of Example 2, compounds such as those of Formulae (II-m) and (II-n) can be synthesized. Similarly, in Step 6 of Example 2, the regent methyl (1S,3R)-3-aminocyclohexane-1-carboxylate can be used in place of methyl (1R,3R)-3-aminocyclohexane-1-carboxylate to obtain compounds of Formulae (II-b) and (II-e). It will be apparent to the skilled reader that by making a combination of these types of modifications to the process set out in Example 2, each of compounds (II-a) to (II-o) depicted above can be synthesized.

Example 3: (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid (462)

Compositions Comprising Compound 462 can be Prepared as Shown in the Scheme Below:

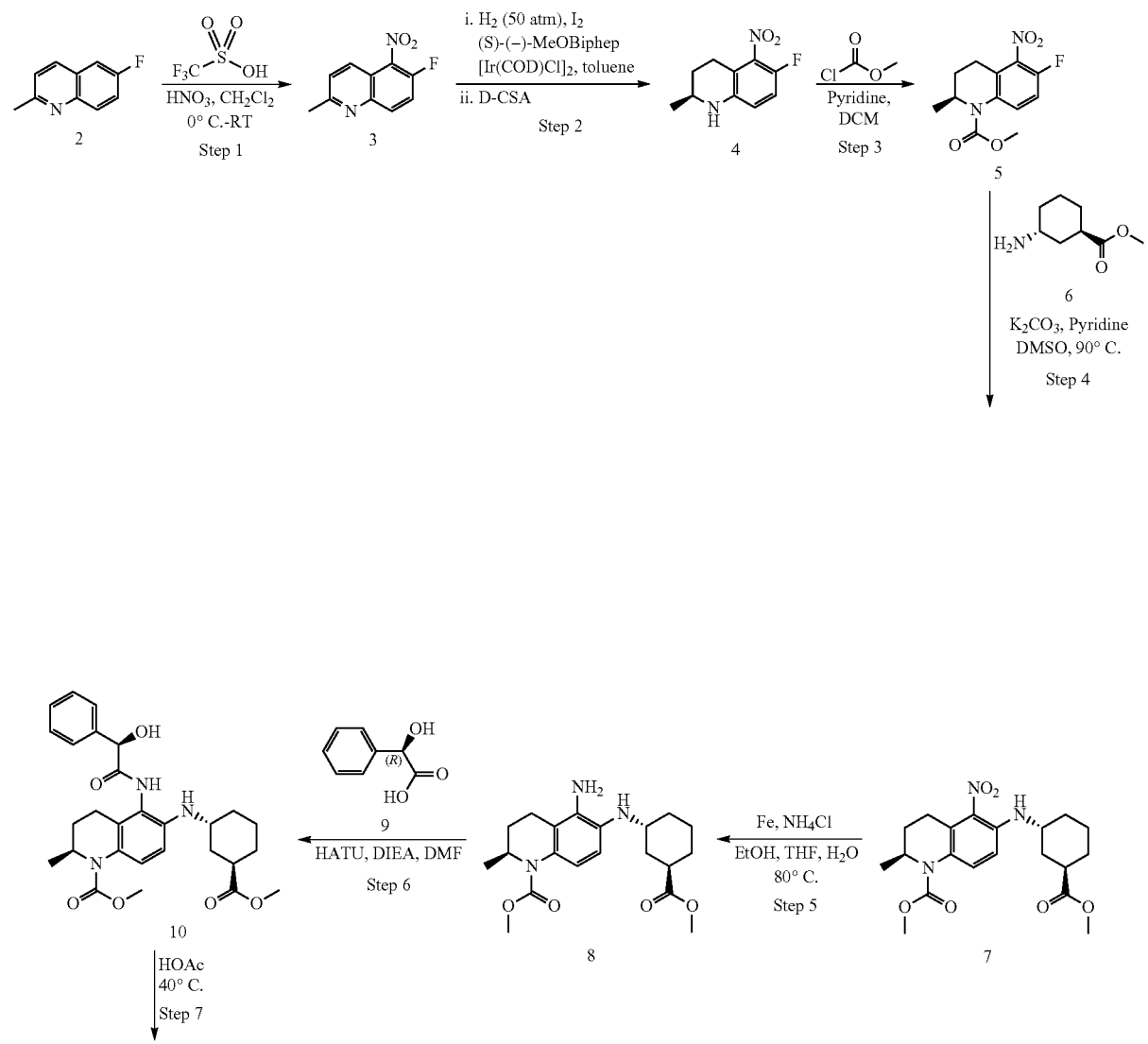

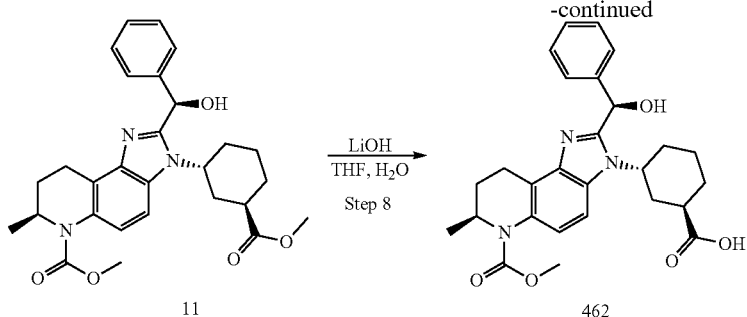

Step 1. 6-fluoro-2-methyl-5-nitroquinoline

A solution of trifluoromethanesulfonic acid (82.0 mL, 0.923 mol) in HNO₃ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]⁺.

Step 2. (2S)-6-fluoro-2-methyl-5-nitro-1,2,3,4-tetrahydroquinoline

A solution of (S)-(−)-MeO-BIPHEP (1.03 mg, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of I₂ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]⁺.

Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1 M hydrogen chloride (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]⁺.

Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 [M+H]⁺.

Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH₄Cl (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]⁺.

Step 6. methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate A solution of (R)-hydroxy-2-phenylacetic acid (972 mg, 6.39 mmol), HATU (1.20 g, 3.16 mmol), methyl (2S)-5-amino-6-[[(1R,3R)-3-(methoxycarbonyl)cyclohexyl]amino]-2-methyl-1,2,3,4-tetrahydroquinoline-1-carboxylate (800 mg, 2.13 mmol), DIEA (1.08 mL, 6.20 mmol) in N,N-dimethylformamide (10 mL) was stirred for 5 h at room temperature (25° C.). The resulting solution was diluted with water (30 mL), and extracted with ethyl acetate (3×50 mL). The organic layers were combined and washed with brine (2×25 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate as a colorless oil (600 mg, 55%). LCMS (ES, m/z): 510 [M+H]$^+$ Step 7. methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate (600 mg, 1.18 mmol) in glacial acetic acid (5 mL, 98%) was stirred for overnight at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 69%) as a colorless oil. LCMS (ES, m/z): 492 [M+H]$^+$.

Step 8. (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 0.81 mmol), LiOH (100 mg, 4.17 mmol) in tetrahydrofuran (5 mL) and water (2 mL) was stirred for overnight at room temperature (25° C.). The resulting mixture was concentrated under vacuum. The crude product was purified by Prep-HPLC (Column: XBridge Shield RP18 OBD Column, 5um, 19×150 mm; Mobile Phase, A: water (containing 10 mmol/L NH$_4$HCO$_3$) and B: ACN (3% to 30% over 21 min); Detector: UV 254 nm). The product fractions were lyophilized to afford (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid as a white solid (83.7 mg, 22%). Enantiomeric excess was determined via HPLC: Column: CHIRALPAK IE-3, Column size: 0.46×5 cm; 3 µm; Mobile phase: Hex (0.1% FA): EtOH=85:15, Flow: 1.0 ml/min. $^1$H-NMR (CD$_3$OD, 400 MHz) δ (ppm): 7.47-7.28 (m, 7H), 6.12 (s, 1H), 4.84-4.74 (m, 2H), 3.79 (s, 3H), 3.33-3.25 (m, 1H), 3.03-2.96 (m, 1H), 2.86-2.82 (m, 1H), 2.38-2.25 (m, 2H), 2.25-2.07 (m, 3H), 1.79-1.72 (m, 1H), 1.64-1.57 (m, 2H), 1.40-1.29 (m, 2H), 1.16 (d, J=6.8 Hz, 3H). LCMS (ES, m/z): 478 [M+H]$^+$; 99.13% ee.

Example 4: (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (452), (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic Acid (515)

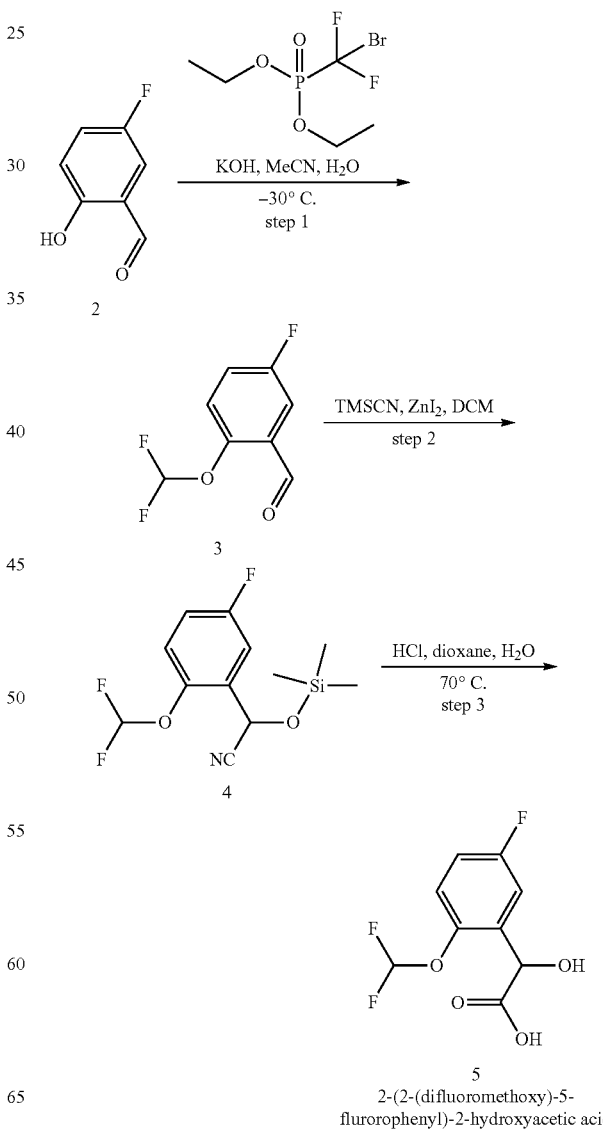

2-(2-(difluoromethoxy)-5-flurorophenyl)-2-hydroxyacetic acid

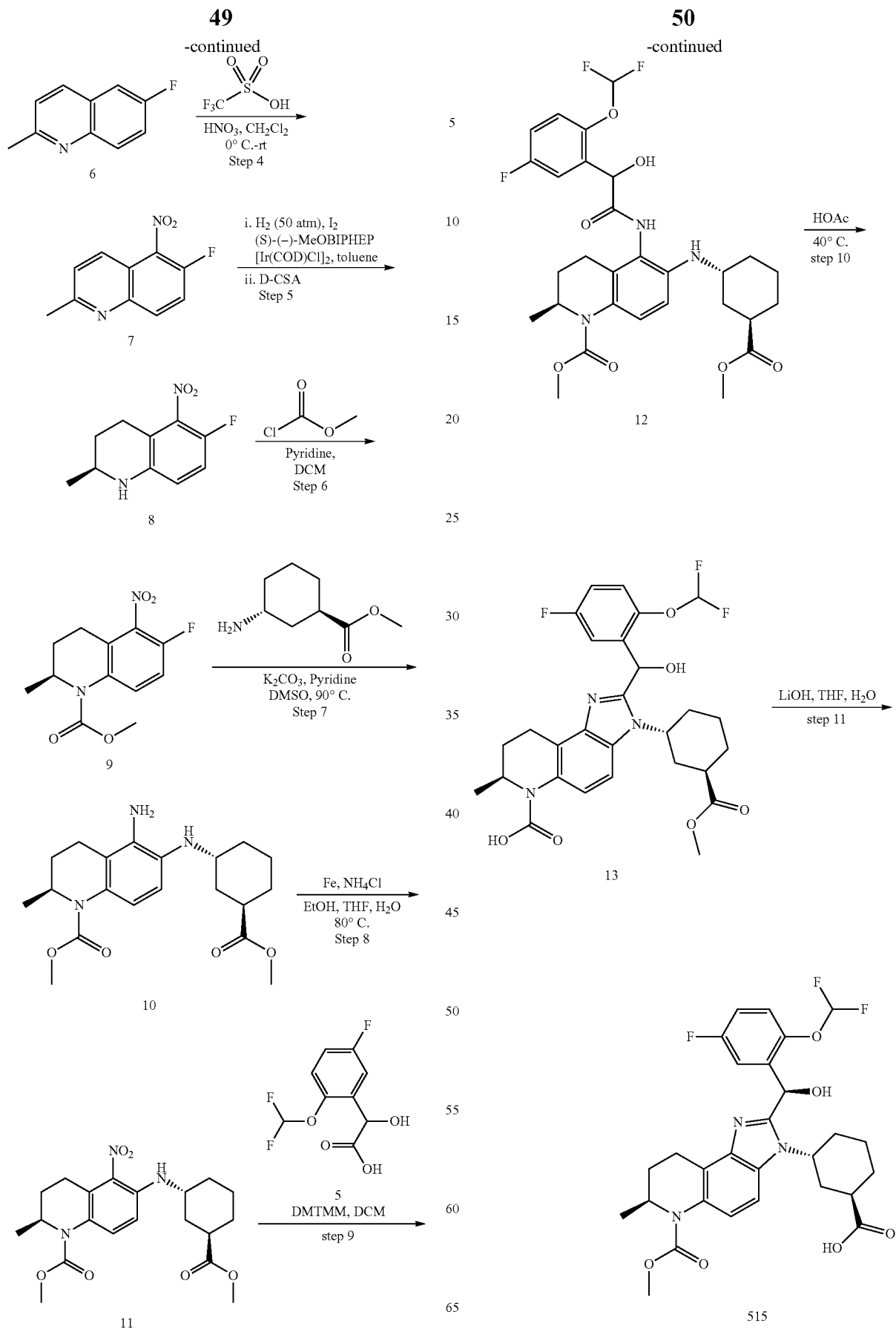

-continued

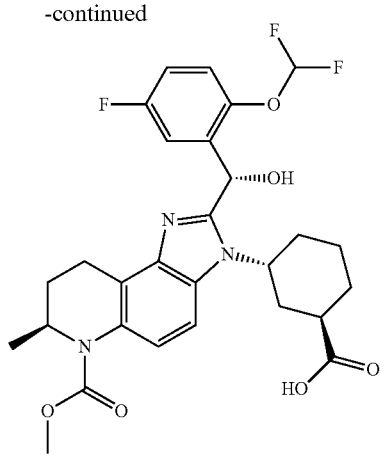

452

Step 1. 2-(difluoromethoxy)-5-fluorobenzaldehyde

A solution of 5-fluoro-2-hydroxybenzaldehyde (2.0 g, 14.3 mmol), diethyl (bromodifluoromethyl)phosphonate (5.69 g, 21.3 mmol), potassium hydroxide (16.0 g, 285 mmol) in MeCN (100 mL) and water (50 mL) was stirred for 1 h at −30° C. The reaction mixture was diluted with water (20 mL). The resulting solution was extracted with ethyl acetate (3×100 mL) and the organic layers combined and dried over anhydrous sodium sulfate. The solids were filtered out. The resulting mixture was concentrated under vacuum. The resulting crude product was purified by silica gel chromatography (eluting with 1:1 ethyl acetate/petroleum ether) to afford 2-(difluoromethoxy)-5-fluorobenzaldehyde as a yellow solid (1.46 g, 54%). LCMS (ES, m/z): 191 [M+H]⁺.

Step 2. 2-[2-(difluoromethoxy)-5-fluorophenyl]-2-[(trimethylsilyl)oxy]acetonitrile A solution of 2-(difluoromethoxy)-5-fluorobenzaldehyde (1.46 g, 7.68 mmol), TMSCN (760 mg, 7.66 mmol), ZnI₂ (50 mg, 0.16 mmol) in dichloromethane (3 mL) was stirred for 2 h at room temperature (25° C.). The resulting mixture was concentrated under vacuum. The resulting crude product was purified by silica gel chromatography (eluting with 1:1 ethyl acetate/petroleum ether) to afford 2-[2-(difluoromethoxy)-5-fluorophenyl]-2-[(trimethylsilyl) oxy]acetonitrile as a yellow solid (800 mg, 36%). LCMS (ES, m/z):290 [M+H]⁺

Step 3. 2-[2-(difluoromethoxy)-5-fluorophenyl]-2-hydroxyacetic Acid

A solution of 2-[2-(difluoromethoxy)-5-fluorophenyl]-2-[(trimethylsilyl)oxy]acetonitrile (800 mg, 2.77 mmol), 1,4-dioxane (2.0 mL), hydrogen chloride (1.0 mL, 12 M) in water (2 mL) was stirred for 12 h at 70° C. and then cooled to room temperature. The resulting solution was concentrated under vacuum. The crude product was purified by reverse phase column chromatography (water (containing 0.05% TFA)/MeCN) to afford 2-[2-(difluoromethoxy)-5-fluorophenyl]-2-hydroxyacetic acid (400 mg, 61%). LCMS (ES, m/z): 237 [M+H]⁺.

Step 4. 6-fluoro-2-methyl-5-nitroquinoline

A solution of trifluoromethanesulfonic acid (82.0 mL, 0.923 mol) in HNO₃ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]⁺.

Step 5. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of I₂ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]⁺.

Step 6. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1 M hydrogen chloride (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]⁺.

Step 7. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2, 3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 [M+H]$^+$.

Step 8. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 9. methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate A solution of methyl (2S)-5-amino-6-[[(1R,3R)-3-(methoxycarbonyl)cyclohexyl]amino]-2-methyl-1,2,3,4-tetrahydroquinoline-1-carboxylate (200 mg, 0.53 mmol), 2-[2-(difluoromethoxy)-5-fluorophenyl]-2-hydroxyacetic acid (220 mg, 0.93 mmol), DMTMM (350 mg, 1.26 mmol) in dichloromethane (5 mL) was stirred for 1 h room temperature (25° C.). The resulting solution was concentrated under vacuum. The resulting crude product was purified by silica gel chromatography (eluting with 1:1 ethyl acetate/petroleum ether) to afford methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate as a yellow solid (70.0 mg, 22%). LCMS (ES, m/z): 594 [M+H]$^+$.

Step 10. methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-[2-(difluoromethoxy)-5-fluorophenyl]-2-hydroxyacetamido]-6-[[((1R,3R)-3-(methoxycarbonyl)cyclohexyl]amino]-2-methyl-1,2,3,4-tetrahydroquinoline-1-carboxylate (70.0 mg, 0.12 mmol) in glacial acetic acid (2.0 mL) was stirred for overnight at 40° C. and then cooled to room temperature. The resulting solution was concentrated under vacuum. The resulting crude product was purified by silica gel chromatography (eluting with 1:2 ethyl acetate/petroleum ether) to afford methyl (7S)-2-[[2-(difluoromethoxy)-5-fluorophenyl](hydroxy)methyl]-3-[(1R,3R)-3-(methoxycarbonyl) cyclohexyl]-7-methyl-3H,6H,7H,8H,9H-imidazo[4,5-f]quinoline-6-carboxylate as a yellow solid (50.0 mg, 74%). LCMS (ES, m/z): 576 [M+H]$^+$.

Step 11. (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid; (1R,3R)-3-[(7S)-2-[(R)-[2-(difluoromethoxy)-5-fluorophenyl](hydroxy) methyl]-6-(methoxycarbonyl)-7-methyl-3H,6H,7H, 8H,9H-imidazo[4,5-f]quinolin-3-yl]cyclohexane-1-carboxylic Acid A solution of methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate (50.0 mg, 0.09 mmol), LiOH (10.0 mg, 0.42 mmol) in tetrahydrofuran (2.0 mL) and water (2.0 mL) was stirred for overnight at room temperature (25° C.). The resulting mixture was concentrated under vacuum. The crude product was purified by Prep-HPLC (Column, XBridge Shield RP18 OBD Column, 30×150 mm, 5 um; Mobile phase, A: water (containing 10 mmol/L NH$_4$HCO$_3$) and B: ACN (25.0% to 35.0% over 8 min); Detector, UV 254/220 nm). The product fractions were concentrated to afford (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (452) as a white solid (4.50 mg, 9%), and (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (515) as a white solid (4.30 mg, 9%). Enantiomeric excess was determined via HPLC: Column: CHIRALPAK IE-3, Column size: 0.46×5 cm; 3 µm; Co-Solvent: IPA (20 mM NH$_3$) Gradient (B %): 10% to 50% in 4.0 min, hold 2.0 min at 50%.

First eluting isomer (452): $^1$H-NMR (CD$_3$OD, 400 MHz) δ (ppm): 7.63-7.61 (m, 1H), 7.53 (d, J=8.8 Hz, 1H), 7.41 (d, J=9.2 Hz, 1H) 7.20-7.13 (m, 2H), 6.67-6.30 (m, 2H), 4.98-4.95 (m, 1H), 4.76-4.71 (m, 1H), 3.78 (s, 3H), 3.15-2.86 (m, 3H), 2.46-2.20 (m, 5H), 1.81-1.53 (m, 5H), 1.13 (d, J=6.8 Hz, 3H). LCMS (ES, m/z): 562 [M+H]$^+$.

Second eluting isomer (515): $^1$H-NMR (CD$_3$OD, 400 MHz) δ (ppm): 7.55-7.53 (m, 1H), 7.47-7.42 (m, 2H), 7.40-7.12 (m, 2H), 6.85-6.44 (m, 2H), 4.94-4.91 (m, 1H), 4.76-4.71 (m, 1H), 3.78 (s, 3H), 3.22-2.84 (m, 3H), 2.46-2.23 (m, 5H), 1.84-1.61 (m, 5H), 1.14 (d, J=6.4 Hz, 3H). LCMS (ES, m/z): 562 [M+H]$^+$; >99.99% ee.

In some embodiments, the disclosure provides the first eluting isomer obtained from Step 11 of the process described in Example 4. In some embodiments, the disclosure provides the second eluting isomer obtained from Step 11 of the process described in Example 4.

Example 5: HTRF Biochemical Assay for CBP and BRD4 Activity

The ability of compounds of formula I to selectively inhibit CBP was determined using the following HTRF biochemical assay for CBP and BRD4 activity. The assay was performed in a final volume of 6 µL in assay buffer containing 50 mM Hepes (pH 7.5, (0.5 M Hepes, pH 7.5 solution; Teknova H1575)), 0.5 mM GSH, 0.01% BGG (0.22 µM filtered, Sigma, G7516-25G), 0.005% BSA (0.22 µM filtered, EMD Millipore Cosporation, 126575) and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 33 µM to 1.7 nM, top to lowest dose, respectively. 3 µL of 2× Protein and 3 µL of 2× Peptide Ligand were added to assay plates (pre-stamped with compound). Plates were incubated for varying times at room temperature prior to measuring the signal. TR-FRET (Time-Resolved Fluorescence Resonance Energy Transfer) was measured on a PHERAstar plate reader (BMG, equipped with HTRF optic module [337/520/490]) or on an Envision plate reader (PerkinElmer, equipped with the TRF Laser unit, TRF dual mirror D400/D505 and emission filters M520 and M495). Data were reported as percent inhibition compared with control wells based on the following equation: % inh=1-((TR-FRET ratio−AveLow)/(AveHigh−AveLow)) where TR-FRET ratio=(Fluorescence at 520 nm/Fluorescence at 490 nm)*10000), AveLow=average TR-FRET ratio of no enzyme control (n=32), and AveHigh=average TR-FRET ratio of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. For all assay formats data were reported as percent inhibition compared with control wells based on the following equation: % inh=100*((FLU−AveLow)/(AveHigh−AveLow)) where FLU=measured Fluorescence, AveLow=average Fluorescence of no enzyme control (n=32), and AveHigh=average Fluorescence of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. $IC_{50}$ values are shown in FIG. 1. As set forth in FIG. 1, an $IC_{50}$ value of less than or equal to 0.01 µM is marked "++++"; a value greater than 0.01 µM and less than or equal to 0.1 µM is marked "+++"; a value greater than 0.1 µM and less than or equal to 1 µM is marked "++"; and values greater than 1 µM is marked "+." Compounds that were not tested in a particular assay are marked "NT."

In some embodiments, the CBP Inhibitor Compound is also selective for CBP activity compared to BRD4 activity, as determined by obtaining a IC50 value for CBP inhibition in the HTRF biochemical assay for CBP that is lower than the corresponding IC50 value obtained for the HTRF biochemical assay for BRD4 activity according to Example 5. A CBP Inhibitor Composition can contain an amount of a compound of the disclosure, or a pharmaceutically acceptable salt thereof, and amounts of one or more stereoisomers of the compound up to amounts that retain sufficient activity of the composition with respect to CBP inhibition and selectivity for CBP over BRD4. Using the methods provided herein, CBP Inhibitor Compositions can contain 95% by HPLC or more of a compound of the disclosure, or a pharmaceutically acceptable salt thereof, and up to 5% by HPLC of one or more stereoisomers of the compound.

In a preferred embodiment, the present disclosure relates to compound 424 having an $IC_{50}$ value of less than or equal to 0.01 µM for the inhibition of CBP, and an $IC_{50}$ value of greater than 0.1 µM and less than or equal to 1 µM for the inhibition of BRD4 as determined by the HTRF biochemical assay for CBP and BRD4 activity described herein in Example 5.

In some embodiments, the present disclosure relates to a compound of Formula (II) selected from the group consisting of compound 424 and its related stereoisomers of structures (II-a) to (II-o) depicted above, having an $IC_{50}$ value of less than or equal to 0.01 µM for the inhibition of CBP, and an $IC_{50}$ value of greater than 0.1 µM and less than or equal to 1 µM for the inhibition of BRD4 as determined by the HTRF biochemical assay for CBP and BRD4 activity described herein in Example 5.

Further embodiments of the disclosure are set out in the following numbered clauses:

1. A compound of formula (III):

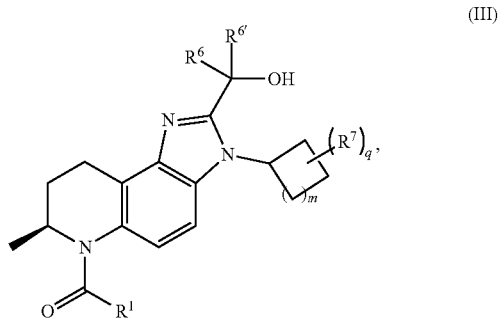

or a pharmaceutically acceptable salt thereof, wherein,
$R^1$ is —$OR^5$;
$R^5$ is —$C_1$-$C_6$ alkyl, —$C_3$-$C_8$ cycloalkyl, heterocyclyl, aryl, or heteroaryl;
$R^6$ is —$C_3$-$C_8$ cycloalkyl, —$C_4$-$C_8$ cycloalkenyl, heterocyclyl, heteroaryl, aryl, wherein each cycloalkyl, cycloalkenyl, heterocyclyl, heteroaryl, or aryl is optionally substituted with one or more —$R^{10}$;
$R^{6'}$ is H or —$C_1$-$C_6$ alkyl;
$R^7$ is —H, halogen, —OH, —CN, —$OC_1$-$C_6$ alkyl, —$NH_2$, —$NHC_1$-$C_6$ alkyl, —$N(C_1$-$C_6$ alkyl$)_2$, —$S(O)_2$$NH(C_1$-$C_6$ alkyl), —$S(O)_2N(C_1$-$C_6$ alkyl$)_2$, —$S(O)_2$$C_1$-$C_6$ alkyl, —$S(O)_2OH$, —$C(O)C_1$-$C_6$ alkyl, —$C(O)$$NH_2$, —$C(O)NH(C_1$-$C_6$ alkyl), —$C(O)N(C_1$-$C_6$ alkyl$)_2$, —$C(O)OH$, —$C(O)OC_1$-$C_6$ alkyl, —$N(C_1$-$C_6$ alkyl$)SO_2C_1$-$C_6$ alkyl, —$S(O)(C_1$-$C_6$ alkyl), —$S(O)N$ $(C_1$-$C_6$ alkyl$)_2$, —$S(O)_2NH_2$, —$N(C_1$-$C_6$ alkyl$)S(O)$ $(C_1$-$C_6$ alkyl) or tetrazole;
$R^{10}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$OC_3$-$C_6$ cycloalkyl, —Oaryl, —Oheteroaryl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —$S(O)_2C_1$-$C_6$ alkyl, —$C(O)C_1$-$C_6$ alkyl, —$C(O)NH_2$, —$C(O)NH(C_1$-$C_6$ alkyl), —$NHC(O)C_1$-$C_6$ alkyl, —$C(O)N(C_1$-$C_6$ alkyl$)_2$, —$C(O)OC_1$-$C_6$ alkyl, —$N(C_1$-$C_6$ alkyl$)SO_2C_1$-$C_6$ alkyl, —$S(O)(C_1$-$C_6$ alkyl), —$S(O)N(C_1$-$C_6$ alkyl$)_2$, or —$N(C_1$-$C_6$ alkyl$)S$ $(O)(C_1$-$C_6$ alkyl), wherein each alkyl, alkenyl, alkynyl, cycloalkyl, cycloalkenyl, heterocyclyl, heteroaryl, or aryl is optionally substituted with one or more —$R^{12}$;
$R^{12}$ is independently, at each occurrence, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, heterocyclyl, heteroaryl, aryl, —OH, halogen, oxo, —$NO_2$, —CN, —$NH_2$, —$OC_1$-$C_6$ alkyl, —$NHC_1$-$C_6$ alkyl, —$N(C_1$-$C_6$ alkyl$)_2$, —$S(O)_2NH(C_1$-$C_6$ alkyl), —$S(O)_2N(C_1$-$C_6$ alkyl$)_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, or —N(C$_1$-C$_6$ alkyl)S(O)(C$_1$-C$_6$ alkyl);

m is an integer from 0 to 5, and q is an integer from 0 to 4.

2. The compound of clause 1, wherein R$^{12}$ is halogen.

3. The compound of any one of clauses 1-2, wherein m is 3.

4. The compound of any one of clauses 1-3, wherein R$^{6'}$ is H.

5. The compound of any one of clauses 1-4, wherein R$^6$ is aryl.

6. The compound of any one of clauses 1-5, wherein R$^7$ is —C(O)OH.

7. The compound of any one of clauses 1-6, wherein R$^5$ is methyl.

8. The compound of clause 1, wherein the compound is of formula (III-c):

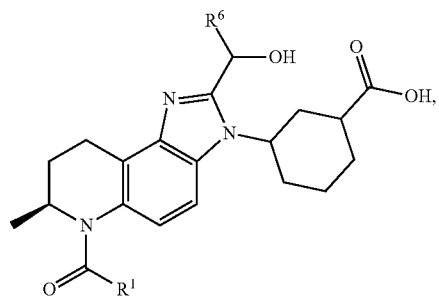

(III-c)

or a pharmaceutically acceptable salt thereof, wherein R$^5$ is —C$_1$-C$_6$ alkyl; and R$^6$ is phenyl optionally substituted with one or more R$^{10}$.

9. The compound of clause 1, wherein the compound is of formula (III-d):

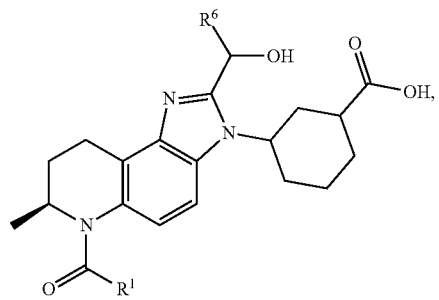

(III-d)

or a pharmaceutically acceptable salt thereof, wherein:
R$^5$ is —C$_1$-C$_3$ alkyl;
R$^6$ is phenyl optionally substituted with one or more R$^{10}$;
R$^{10}$ is independently, at each occurrence halogen, —OC$_1$-C$_6$ alkyl, —OC$_3$-C$_6$ cycloalkyl, -Oaryl, or —Ohet-eroaryl, wherein each alkyl, cycloalkyl, aryl or heteroaryl is optionally substituted with one or more —R$^{12}$; and R$^{12}$ is halogen.

10. The compound of any one of clauses 1-7, wherein R$^6$ is aryl optionally substituted with one or more R$^{10}$.

11. The compound of any one of clauses 1-7, wherein R$^6$ is phenyl optionally substituted with one or more R$^{10}$.

12. The compound of any one of clauses 1-6, 8 or 10-11, wherein R$^5$ is —C$_1$-C$_3$ alkyl.

13. The compound of any one of clauses 1-6 or 8-12, wherein R$^5$ is methyl.

14. The compound of any one of clauses 1-13, wherein R$^{10}$ is independently, at each occurrence, halogen or —OC$_1$-C$_6$ alkyl, wherein —OC$_1$-C$_6$ alkyl is optionally substituted with halogen.

15. A pharmaceutical composition comprising a compound of any one of clauses 1-14 or a pharmaceutically acceptable salt thereof and a pharmaceutically acceptable carrier.

What is claimed is:
1. A compound according to the following formula:

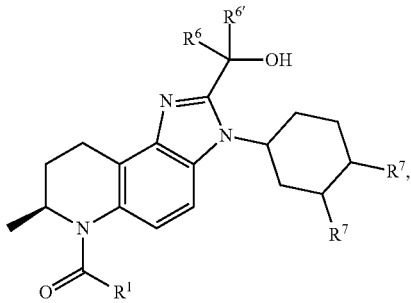

or a pharmaceutically acceptable salt or enantiomer thereof, wherein:
R$^1$ is —OR$^5$;
R$^5$ is —C$_1$-C$_6$ alkyl, —C$_3$-C$_8$ cycloalkyl, heterocyclyl, aryl, or heteroaryl;
R$^6$ is —C$_3$-C$_8$ cycloalkyl, —C$_4$-C$_8$ cycloalkenyl, heterocyclyl, heteroaryl, aryl, wherein each cycloalkyl, cycloalkenyl, heterocyclyl, heteroaryl, or aryl is optionally substituted with one or more —R$^{10}$;
R$^{6'}$ is —C$_1$-C$_6$ alkyl-C$_1$-C$_2$ alkyl;
R$^7$ is —H at one occurrence, and —C(O)OH or —C(O)OC$_1$-C$_6$ alkyl at the other occurrence;
R$^{10}$ is independently, at each occurrence, —C$_1$-C$_6$ alkyl, —C$_2$-C$_6$ alkenyl, —C$_2$-C$_6$ alkynyl, —C$_3$-C$_6$ cycloalkyl, —C$_4$-C$_8$ cycloalkenyl, heterocyclyl, heteroaryl, aryl, —OH, halogen, oxo, —NO$_2$, —CN, —NH$_2$, —OC$_1$-C$_6$ alkyl, —OC$_3$-C$_6$cycloalkyl, -Oaryl, -Ohet-eroaryl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —NHC(O)C$_1$-C$_6$ alkyl, —C(O)N(C$_1$-C$_6$ alkyl)$_2$, —C(O)OC$_1$-C$_6$ alkyl, —N(C$_1$-C$_6$ alkyl)SO$_2$C$_1$-C$_6$ alkyl, —S(O) (C$_1$-C$_6$ alkyl), —S(O)N(C$_1$-C$_6$ alkyl)$_2$, or —N(C$_1$-C$_6$ alkyl)S(O)(C$_1$-C$_6$ alkyl), wherein each alkyl, alkenyl, alkynyl, cycloalkyl, cycloalkenyl, heterocyclyl, heteroaryl, or aryl is optionally substituted with one or more —R$^{12}$; and
R$^{12}$ is independently, at each occurrence, —C$_1$-C$_6$ alkyl, —C$_2$-C$_6$ alkenyl, —C$_2$-C$_6$ alkynyl, —C$_3$-C$_8$ cycloalkyl, —C$_4$-C$_8$ cycloalkenyl, heterocyclyl, heteroaryl, aryl, —OH, halogen, oxo, —NO$_2$, —CN, —NH$_2$, —OC$_1$-C$_6$ alkyl, —NHC$_1$-C$_6$ alkyl, —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —C(O)OC$_1$-C$_6$ alkyl, —N(C$_1$-C$_6$ alkyl) SO$_2$C$_1$-C$_6$ alkyl, —S(O) (C$_1$-C$_6$ alkyl), —S(O)N(C$_1$-C$_6$ alkyl)$_2$, or —N(C$_1$-C$_6$ alkyl)S(O)(C$_1$-C$_6$ alkyl).

2. The compound of claim 1, wherein $R^5$ is —$C_1$-$C_6$ alkyl.
3. The compound of claim 1, wherein $R^5$ is methyl.
4. The compound of claim 1, wherein q is 1.
5. The compound of claim 1, wherein $R^7$ is —H at one occurrence and —C(O)OH at the other occurrence.
6. The compound of claim 1, wherein m is 3, q is 1, and $R^7$ is —C(O) OH.
7. The compound of claim 1, wherein $R^{6'}$ is —$C_1$-$C_3$ alkyl.
8. The compound of any one of claim 1, wherein $R^{6'}$ is selected from methyl and ethyl.
9. The compound of claim 1, wherein $R^6$ is selected from aryl and heteroaryl, and each aryl or heteroaryl is optionally substituted with one or more —$R^{10}$.
10. The compound of claim 1, wherein each $R^{10}$ is independently selected from halogen and —$OC_1$-$C_6$ alkyl.
11. The compound of claim 1, wherein each $R^{10}$ is independently selected from F and —$OCH_3$.
12. The compound of claim 1, selected from the group consisting of:

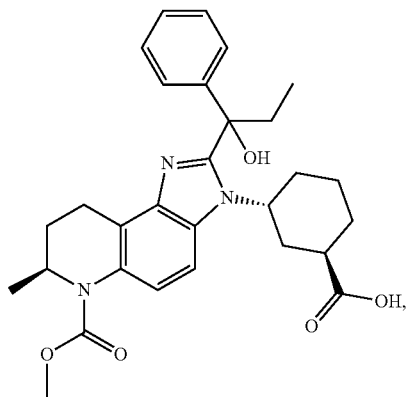

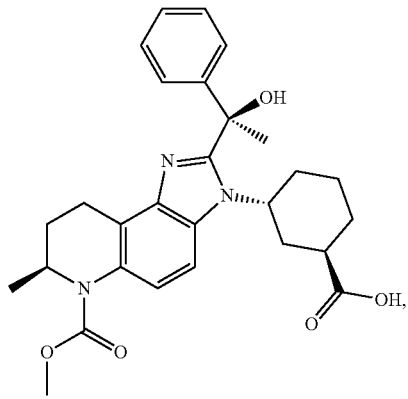

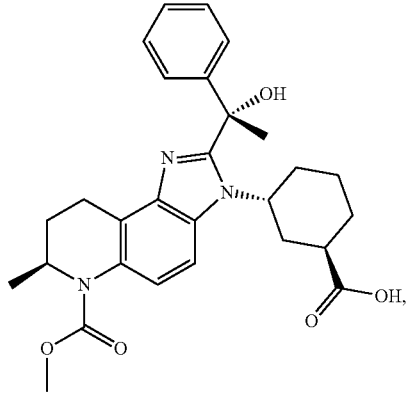

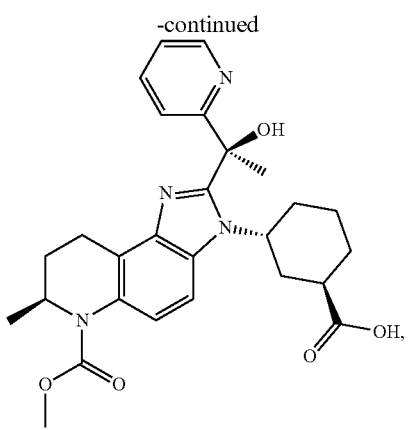

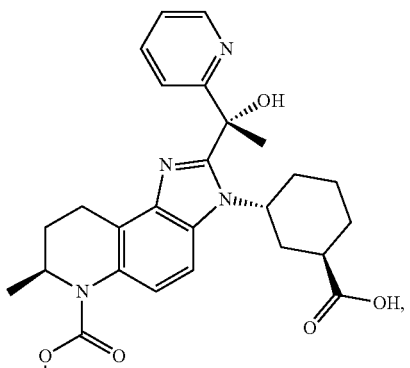

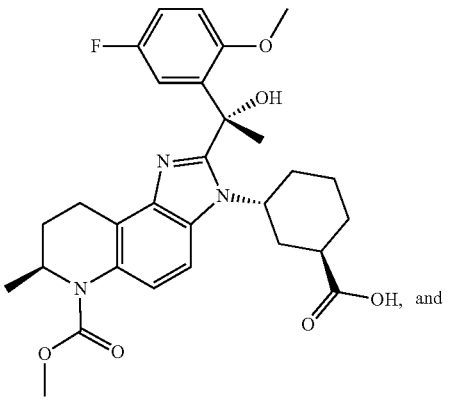

, and

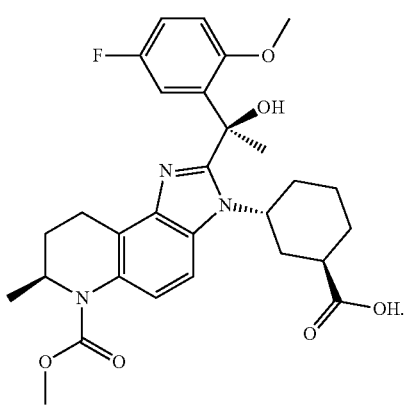

.

13. A compound selected from the group consisting of:
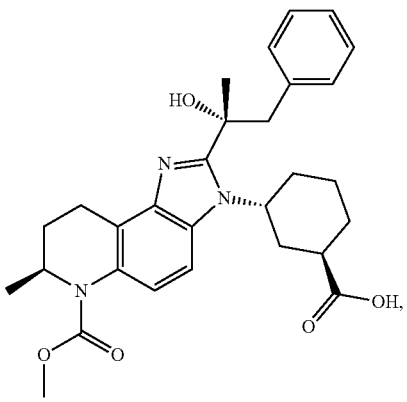
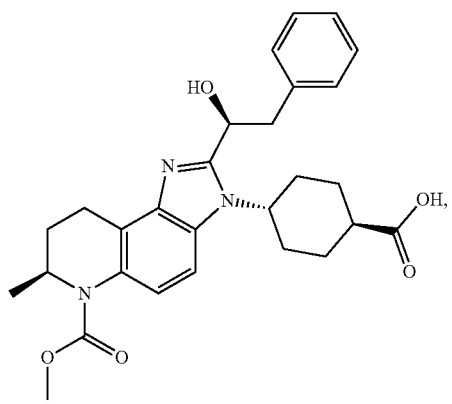
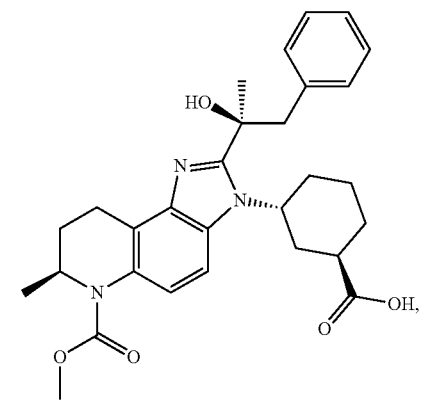
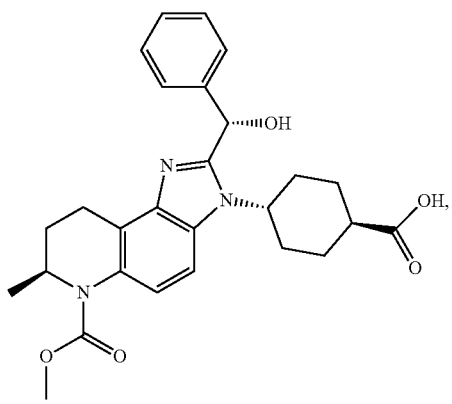
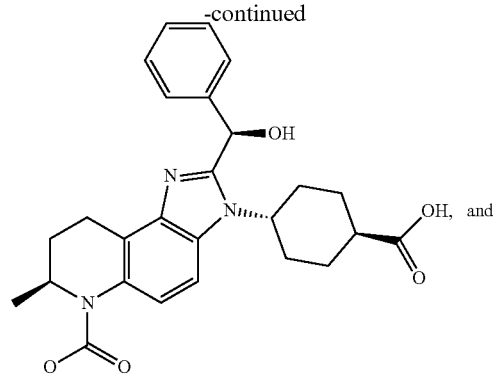
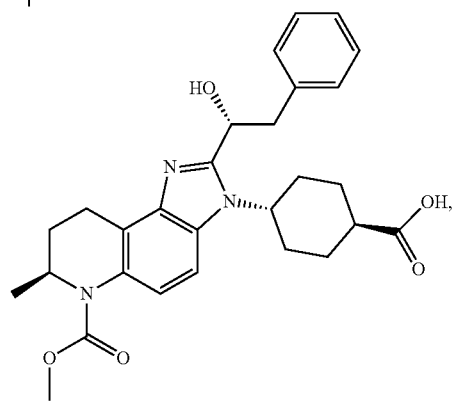
or a pharmaceutically acceptable salt thereof.
14. A compound selected from the group consisting of:
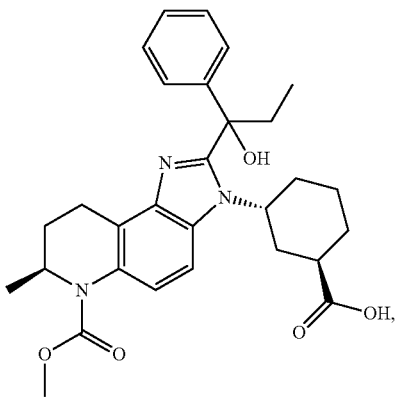
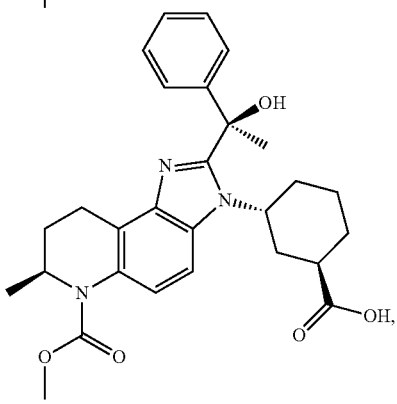

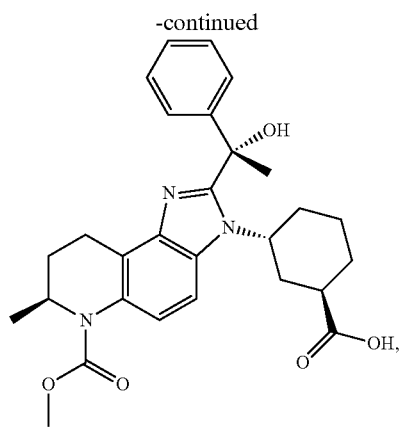
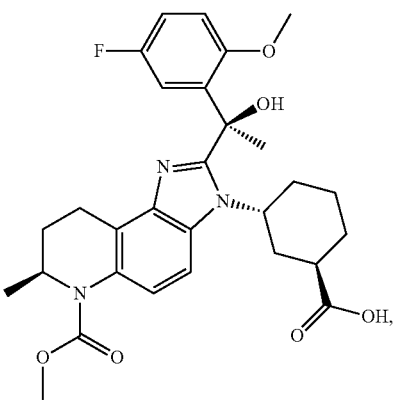
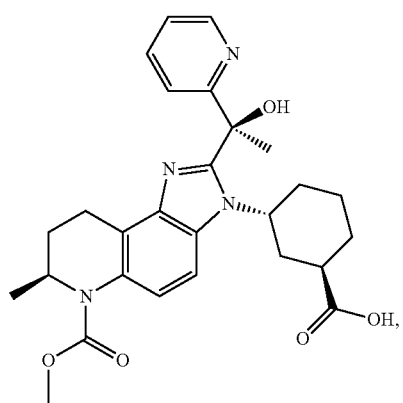
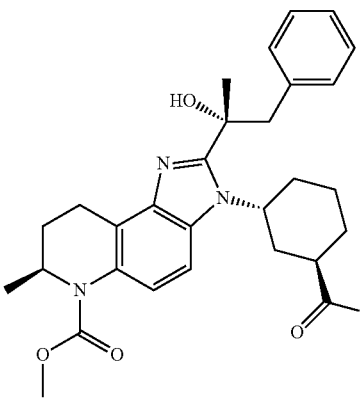
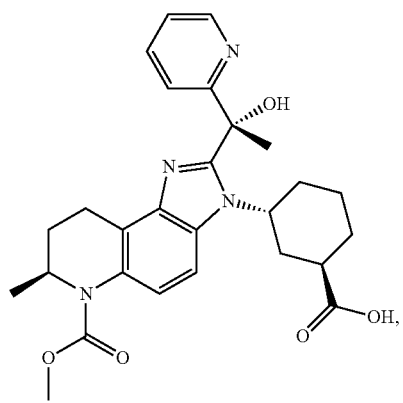
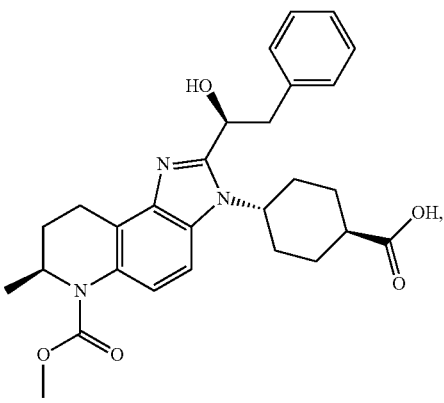 [SMILES: COC(=O)N1c2ccc3c(nc([C@H](O)Cc4ccccc4)n3[C@H]3CC[C@H](C(=O)O)CC3)c2CC[C@@H]1C]
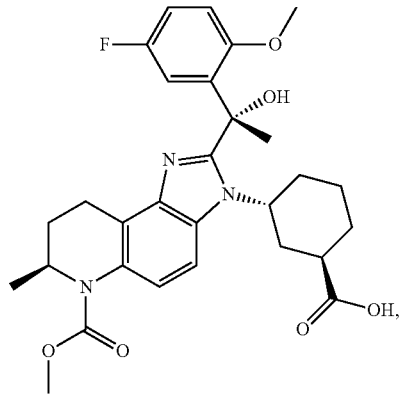
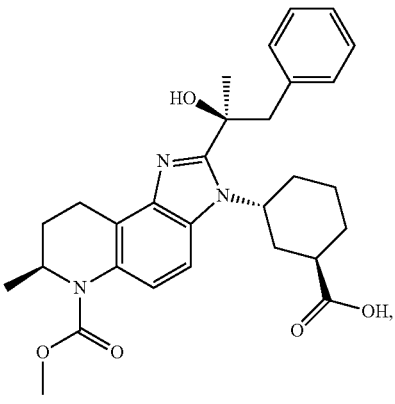

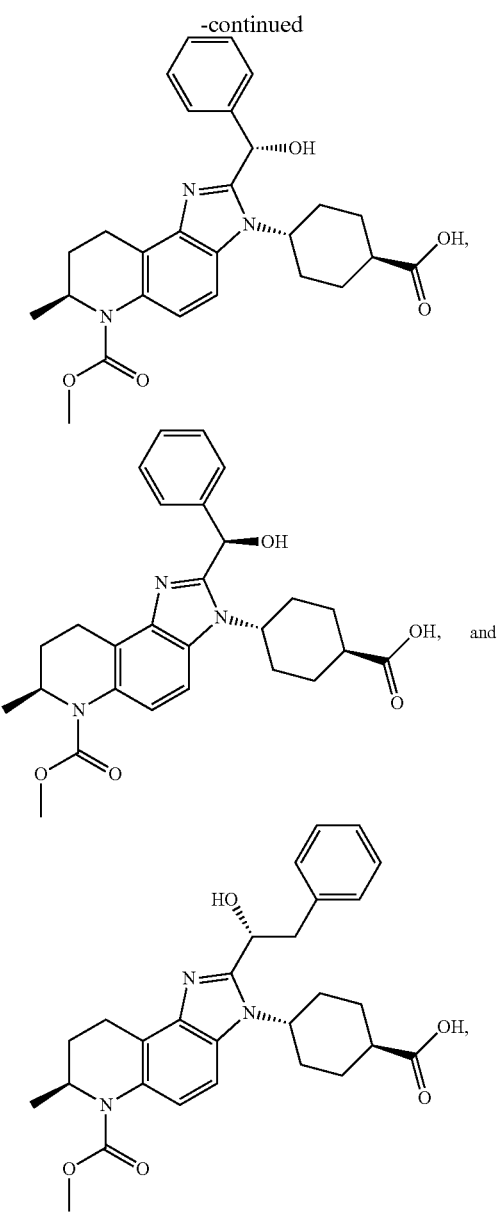
or a pharmaceutically acceptable salt thereof.
15. The compound of claim 14, wherein the compound is:
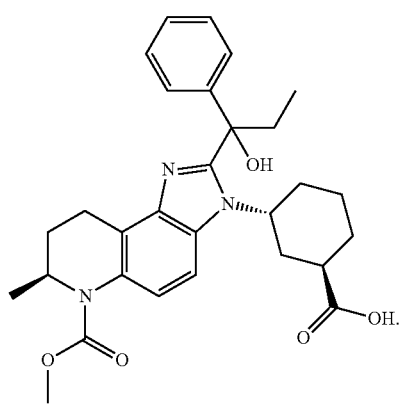 [SMILES: CCC(O)(c1ccccc1)c1nc2c3c(ccc2n1[C@@H]1CCC[C@@H](C(=O)O)C1)N(C(=O)OC)[C@@H](C)CC3]
16. The compound of claim 14, wherein the compound is:
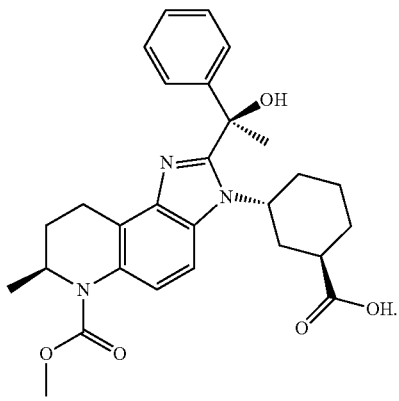 [SMILES: COC(=O)N1c2ccc3c(nc([C@](C)(O)c4ccccc4)n3[C@@H]3CCC[C@@H](C(=O)O)C3)c2CC[C@@H]1C]
17. The compound of claim 14, wherein the compound is:
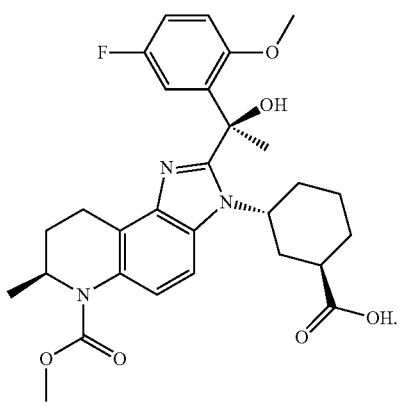 [SMILES: COC(=O)N1c2ccc3c(nc([C@](C)(O)c4cc(F)ccc4OC)n3[C@@H]3CCC[C@@H](C(=O)O)C3)c2CC[C@@H]1C]
18. The compound of claim 14, wherein the compound is:
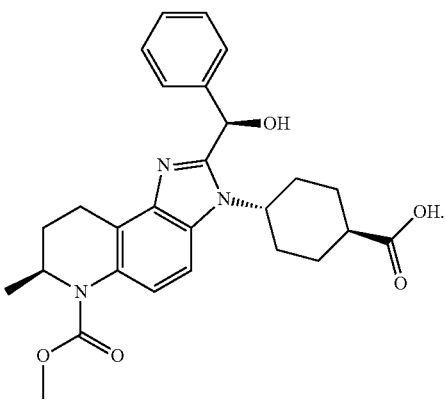 [SMILES: COC(=O)N1c2ccc3c(nc([C@H](O)c4ccccc4)n3[C@H]3CC[C@H](C(=O)O)CC3)c2CC[C@@H]1C]
19. A pharmaceutical composition comprising the compound of claim 14, or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 12,378,242 B2 |
| APPLICATION NO. | : 17/669112 |
| DATED | : August 5, 2025 |
| INVENTOR(S) | : Shawn E. R. Schiller et al. |

It is certified that error appears in the above-identified patent and that said Letters Patent is hereby corrected as shown below:

In the Claims

Column 58, Line 39, Claim 1, "$R^{6'}$ is $-C_1-C_6$ alkyl-$C_1-C_2$ alkyl" should be --$R^{6'}$ is $-C_1-C_2$ alkyl--.

Column 58, Lines 43-44, Claim 1, "$-C_3-C_6$ cycloalkyl" should be -- $-C_3-C_8$ cycloalkyl--.

Signed and Sealed this
Eleventh Day of November, 2025

John A. Squires
*Director of the United States Patent and Trademark Office*